United States Patent
Holman et al.

(10) Patent No.: US 11,774,451 B2
(45) Date of Patent: Oct. 3, 2023

(54) MOLECULAR VIBRATIONAL SPECTROSCOPIC MARKERS FOR DETECTION OF CANCER

(71) Applicant: The Board of Trustees of the Leland Stanford Junior University, Stanford, CA (US)

(72) Inventors: Derek Holman, Redwood City, CA (US); Francis G. Blankenberg, Portola Valley, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 324 days.

(21) Appl. No.: 17/095,304

(22) Filed: Nov. 11, 2020

(65) Prior Publication Data
US 2021/0156862 A1 May 27, 2021

Related U.S. Application Data

(60) Provisional application No. 62/938,564, filed on Nov. 21, 2019.

(51) Int. Cl.
| | | |
|---|---|---|
| C12N 15/10 | (2006.01) |
| B01L 3/00 | (2006.01) |
| G01N 21/3504 | (2014.01) |
| G01N 33/00 | (2006.01) |
| G01N 33/574 | (2006.01) |
| G01N 21/64 | (2006.01) |

(Continued)

(52) U.S. Cl.
CPC ....... *G01N 33/57449* (2013.01); *A61K 45/06* (2013.01); *G01N 21/6486* (2013.01); *G01N 2021/3595* (2013.01)

(58) Field of Classification Search
CPC ......... G01N 33/57449; G01N 21/6486; G01N 2021/3595; G01N 21/35; G01N 21/39; G01N 2201/129; A61K 45/06
See application file for complete search history.

(56) References Cited

U.S. PATENT DOCUMENTS

| 4,816,567 A | 3/1989 | Cabilly et al. |
| 2005/0163711 A1* | 7/2005 | Nycz ................... A61P 15/00 424/9.1 |

(Continued)

FOREIGN PATENT DOCUMENTS

| GB | 2276169 | 9/1994 |
| WO | WO-2016097996 A1 * | 6/2016 |

OTHER PUBLICATIONS https://www.rp-photonics.com/diffraction_limited_beams.html (Year: 2019).*

(Continued)

*Primary Examiner* — Jennifer Wecker
*Assistant Examiner* — Oyeleye Alexander Alabi
(74) *Attorney, Agent, or Firm* — Pamela J. Sherwood; Bozicevic, Field & Francis LLP

(57) ABSTRACT

Methods of detecting diagnostic biomarkers on cancer-derived extracellular vesicles such as exosomes by mid-infrared spectroscopy are provided. In particular, methods of detecting ovarian cancer by spectral fingerprint analysis of molecular vibrational spectroscopic markers on individual or subpopulations of extracellular vesicles are disclosed.

18 Claims, 8 Drawing Sheets

(51) Int. Cl.
*A61K 45/06* (2006.01)
*G01N 21/35* (2014.01)

(56) References Cited

U.S. PATENT DOCUMENTS

| 2012/0077263 | A1  | 3/2012 | Ward et al. |
| 2020/0102312 | A1* | 4/2020 | Chiosis ............... A61P 3/10 |
| 2022/0275091 | A1* | 9/2022 | Doyle ............... A61P 25/00 |

OTHER PUBLICATIONS

Beekman et al. (2019) "Immuno-capture of extracellular vesicles for individual multi-modal characterization using AFM, SEM and Raman spectroscopy." Lab on a Chip 19.15 2526-2536.

Blankenberg et al. (1999) "Imaging of apoptosis (programmed cell death) with 99mTc annexin V". J Nucl Med. Jan. 1999;40(1):184-91. PMID: 9935075.

Caby et al. (2005) "Exosomal-like vesicles are present in human blood plasma." International immunology 17.7, 879-887.

Funaki et al. (2001) "Membrane fluidity correlates with liver cancer cell proliferation and infiltration potential." Oncology reports 8.3, 527-532.

Grzelak et al. (2018) "Diagnosis of ovarian tumour tissues by SR-FTIR spectroscopy: A pilot study." Spectrochimica Acta Part A: Molecular and Biomolecular Spectroscopy 203, 48-55.

Kim et al. (2018) "None of us is the same as all of us: resolving the heterogeneity of extracellular vesicles using single-vesicle, nanoscale characterization with resonance enhanced atomic force microscope infrared spectroscopy (AFM-IR)." Nanoscale Horizons 3.4, 430-438.

Lea et al. (2017) "Detection of phosphatidylserine-positive exosomes as a diagnostic marker for ovarian malignancies: a proof of concept study." Oncotarget 8.9, 14395.

Li et al. (2018) "Characterization of ovarian cancer cells and tissues by Fourier transform infrared spectroscopy." Journal of ovarian research 11.1, 64.

Liu et al. (2017) "The Exosome Total Isolation Chip". ACS Nano. Nov. 28, 2017;11(11):10712-10723. PMID: 29090896.

* cited by examiner

MOLECULAR VIBRATIONAL SPECTROSCOPIC MARKERS FOR DETECTION OF CANCER

CROSS REFERENCE

This application claims benefit of U.S. Provisional Patent Application No. 62/938,564 filed Nov. 21, 2019. This application is incorporated herein by reference its entirety.

BACKGROUND

Early detection of cancer drastically increases the probability of successful treatment. For example, while the 5-year survival of patients with late stage ovarian carcinoma is less than 50%, the 5-year survival of patients with localized ovarian carcinoma is over 90%. However, due to a lack of effective screening modalities, fewer than 15% of ovarian cancer diagnoses are made at an early stage when the tumor is still localized. Existing methods for screening of ovarian carcinoma, including pelvic ultrasound, magnetic resonance imaging (MRI), and monitoring carbohydrate antigen 125 (CA-125) levels in combination with peripheral blood proteomics (Lea et al. (2017) Oncotarget 8(9):14395-14407) have failed in clinical trials to improve the survival rate of women with ovarian cancer.

Therefore, identification of reliable biomarkers and diagnostic methods that would allow earlier cancer detection and monitoring of treatment is urgently needed to improve survival rates.

SUMMARY

Methods of detecting and quantitating biomarkers on cancer-derived extracellular vesicles are provided. In certain embodiments, methods of detecting ovarian cancer with molecular vibrational spectroscopic markers using mid-infrared spectroscopy are disclosed.

In one aspect, a method for diagnosing a patient suspected of having cancer is provided, the method comprising: a) obtaining a biological sample comprising extracellular vesicles from the patient; b) recording a mid-infrared spectrum of a single cancer-derived extracellular vesicle or a subpopulation of cancer-derived extracellular vesicles, if present, in the biological sample; c) diagnosing the patient based on analysis of the mid-infrared spectrum, wherein detection of a spectral chemical fingerprint for one or more cancer biomarkers from the single cancer-derived extracellular vesicle or the subpopulation of cancer-derived extracellular vesicles, if present, indicates that the patient is has cancer or is at risk of having cancer. In one embodiment, the cancer is ovarian cancer.

In certain embodiments, the subject methods are used to detect a new cancer (i.e., not previously diagnosed), monitor treatment of a cancer (i.e., previously diagnosed), or detect progression or a recurrence of a cancer in a patient.

In some embodiments, the method further comprises medical imaging of the patient to confirm diagnosis of the cancer or recurrence of the cancer if the mid-infrared spectral chemical fingerprint indicates the presence of a cancer-derived extracellular vesicle and that the patient is at risk of having cancer. Exemplary medical imaging techniques include, without limitation, radiography, radiography, magnetic resonance imaging (MRI), ultrasound, photoacoustic imaging, computed tomography (CT), positron emission tomography (PET), single-photon emission computed tomography (SPECT), endoscopy, optical imaging, fluorescence imaging, elastography, and thermography. In some embodiments, medical imaging is used to locate a primary, metastatic, or recurrent tumor in a patient after diagnosing the patient as being at risk of having cancer based on the spectral chemical fingerprint for one or more cancer biomarkers from a cancer-derived extracellular vesicle or subpopulation of cancer-derived extracellular vesicles.

In certain embodiments, the method further comprises performing a biopsy, laparoscopy, or surgical resection of the cancer.

In some embodiments, the method further comprises treating the patient for the cancer if the patient has a positive diagnosis for the cancer based on the spectral chemical fingerprint for one or more cancer biomarkers from a cancer-derived extracellular vesicle or subpopulation of cancer-derived extracellular vesicles and confirmation of a positive cancer diagnosis by medical imaging, biopsy, laparoscopy, or other method of cancer diagnosis. Exemplary methods of treatment include, without limitation, surgery, radiation therapy, chemotherapy, targeted therapy, anti-angiogenic therapy, or immunotherapy, or any combination thereof.

In certain embodiments, cancer risk is determined by detection of individual cancer-derived extracellular vesicles. Bulk sampling methods which average signal over the whole sample population are much less effective in evaluating cancer risk. In certain embodiments, the method further comprises dispersing the cancer-derived extracellular vesicles. Dispersing the extracellular vesicles permits the detection and characterization of individual cancer-derived extracellular vesicles and subpopulations of cancer-derived extracellular vesicles in the biological sample. In some embodiments, after dispersing the cancer-derived extracellular vesicles, the mid-infrared spectrum of a single cancer-derived extracellular vesicle or a subpopulation of cancer-derived extracellular vesicles is recorded. In some embodiments, the method further comprises detecting individual cancer-derived extracellular vesicles in subpopulations of the extracellular vesicles in the sample. In certain embodiments, the cancer-derived extracellular vesicles in the sample are sufficiently dispersed to allow imaging of a single cancer-derived extracellular vesicle. Exosomes can be dispersed, for example, in the presence of annexin V and $Ca^{2+}$ (e.g., $CaCl_2$) or $Ca^{2+}$ without annexin V for single-exosome imaging. In some embodiments, the extracellular vesicles are substantially purified prior to imaging.

In certain embodiments, detection of the spectral chemical fingerprint comprises comparing the spectrum of the cancer-derived extracellular vesicle or a subpopulation of cancer-derived extracellular vesicles from the biological sample to a reference mid-infrared spectrum of a reference cancer-derived extracellular vesicle obtained from a subject with cancer to determine if the spectrum of the cancer-derived extracellular vesicle or the subpopulation of cancer-derived extracellular vesicles from the biological sample matches the reference spectrum in a spectral region corresponding to the spectral chemical fingerprint. In certain embodiments, the cancer is ovarian cancer, and the reference mid-infrared spectrum is of a reference sample obtained from a subject with early stage ovarian cancer (i.e., stage I or stage II) or late stage ovarian cancer (i.e., stage III or stage IV) to allow an estimation of the cancer stage of the patient.

In certain embodiments, the method further comprises comparing the mid-infrared spectrum of the biological sample to a control mid-infrared spectrum of a sample obtained from a control subject not having the cancer, wherein the spectral chemical fingerprint comprises at least one spectral difference between the spectrum of the biological sample and the spectrum of the control sample. In other embodiments, the method further comprises comparing the mid-infrared spectrum of a single cancer-derived extracellular vesicle or a subpopulation of cancer-derived extracellular vesicles to a control mid-infrared spectrum of a control extracellular vesicle, wherein the spectral chemical fingerprint comprises at least one spectral difference between the spectrum of the cancer-derived extracellular vesicle or subpopulation of cancer-derived extracellular vesicles from the biological sample and the spectrum of the control extracellular vesicle. A spectral difference may include, for example, without limitation, an increase or decrease in absorbance at a same wavenumber or a shift in position of an absorption peak in the mid-infrared spectrum of the biological sample compared to the control mid-infrared spectrum. In certain embodiments, the spectral difference is in a spectral region ranging between wavenumbers from about 2800 $cm^{-1}$ to about 3000 $cm^{-1}$, about 1500 $cm^{-1}$ to about 1750 $cm^{-1}$, or about 900 $cm^{-1}$ to about 1300 $cm^{-1}$.

In certain embodiments, detection of the spectral chemical fingerprint is automated by using a multivariate classification algorithm.

The methods described herein can be applied to extracellular vesicles including, but not limited to, exosomes, ectosomes, microparticles, microvesicles, and nanosomes.

In certain embodiments, a patient, diagnosed as having cancer (e.g., ovarian cancer) by the methods described herein, is treated with surgery, radiation therapy, chemotherapy, targeted therapy, anti-angiogenic therapy, immunotherapy, or any combination thereof.

In certain embodiments, the one or more cancer biomarkers comprise lipids, membrane-bound proteins, or adsorbed proteins on the cancer-derived extracellular vesicle. In some embodiments, the one or more biomarkers are cancer cell-specific proteins. In some embodiments, at least one biomarker is an exosome surface marker. In some embodiments, at least one biomarker is a metabolite.

In certain embodiments, the method further comprises performing an immunoassay to detect one or more biomarkers. Exemplary immunoassay techniques include, without limitation, an enzyme-linked immunosorbent assay (ELISA), an immunofluorescent assay (IFA), an immune-polymerase chain reaction assay, an electro-chemiluminescence immunoassay (ECLIA), and a radioimmunoassay (RIA).

In certain embodiments, the one or more cancer biomarkers comprise phosphatidylserine, wherein an increased level of the phosphatidylserine in the cancer-derived extracellular vesicle membrane compared to a control level of the phosphatidylserine indicates that the patient has cancer.

In certain embodiments, the method further comprises contacting the extracellular vesicles in the biological sample with a phosphatidylserine binding agent such that the phosphatidylserine binding agent binds to the phosphatidylserine in the membranes of the extracellular vesicles. The phosphatidylserine positive cancer-derived extracellular vesicle can be isolated by positive selection for extracellular vesicles comprising the phosphatidylserine binding agent bound to the phosphatidylserine. In some embodiments, the phosphatidylserine binding agent is detectably labeled, for example, with a detectable label including without limitation, a fluorescent label, a chemiluminescent label, a bioluminescent label, or an isotopic label. A phosphatidylserine positive cancer-derived extracellular vesicle comprising the bound phosphatidylserine binding agent comprising the fluorescent label can be isolated, for example, by fluorescence-associated cell sorting (FACS). In certain embodiments, the phosphatidylserine is detected by using mid-Infrared vibrational spectroscopy to detect increases in membrane stiffness or bilayer deformation caused by binding of the phosphatidylserine binding agent to the phosphatidylserine. In some embodiments, the phosphatidylserine binding agent is a protein, peptide, aptamer, antibody, or small molecule that binds to phosphatidylserine. In one embodiment, the phosphatidylserine binding agent is annexin V or an annexin V mimetic.

In certain embodiments, the extracellular vesicles are not lysed or permeabilized.

In certain embodiments, mid-Infrared vibrational spectroscopy is performed with a narrow-band mid-infrared light source or a broadband mid-infrared light source. For example, a narrow-band mid-infrared light source may include, without limitation, a quantum cascade laser-based device. A broadband mid-infrared light source may include, without limitation, a synchrotron source.

In certain embodiments, the mid-infrared spectrum is recorded using an atomic force microscope Fourier transform infrared (AFM-FTIR) spectrometer. In some embodiments, an AFM probe is used to detect a single cancer-derived extracellular vesicle.

In certain embodiments, the mid-infrared spectrum is recorded using synchrotron infrared nanospectroscopy (SINS).

In certain embodiments, the mid-infrared spectrum is recorded using infrared spectroscopy performed with a diffraction-limited laser beam focused on a single cancer-derived extracellular vesicle. In some embodiments, the method further comprises loading at least a portion of the extracellular vesicles from the biological sample into a microfluidic device, and focusing the diffraction-limited laser beam on a single cancer-derived extracellular vesicle in the microfluidic device. For example, the diffraction-limited laser beam can be focused on a single cancer-derived extracellular vesicle in a microfluidic channel or chamber of the microfluidic device.

In certain embodiments, one or more biomarkers are lipids, or membrane-bound proteins or adsorbed proteins on the extracellular vesicles. In one embodiment, at least one biomarker is an extracellular vesicle surface marker. In another embodiment, one or more biomarkers are cancer cell-specific proteins. In yet another embodiment, at least one biomarker is a metabolite.

The methods of the invention can be combined with any other methods known in the art for detecting, quantitating, isolating, identifying, or further characterizing biomarkers, for example, including without limitation, flow cytometry, fluorescence-associated cell sorting (FACS), immunohistochemistry, enzyme-linked immunosorbent assay (ELISA), immunofluorescent assay (IFA), immune-polymerase chain reaction assay, electro-chemiluminescence immunoassay (ECLIA), radioimmunoassay (RIA), mass spectrometry, and sequencing.

In another embodiment, the patient is human.

In certain embodiments, the method further comprises comparing the mid-infrared spectrum of the single cancer-derived extracellular vesicle or the subpopulation of cancer-derived extracellular vesicles from the biological sample to a mid-infrared spectrum of a single extracellular vesicle or a subpopulation of extracellular vesicles from a sample obtained from the patient at an earlier timepoint.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 4A shows surface anchoring and reduction of $NO_2$-functionalized N-heterocyclic carbene molecules (NHCs) on Au particles. FIG. 4B shows Infrared nanospectroscopy measurements on $NO_2$-functionalized NHCs on Au particles. FIG. 4C shows $NO_2$-functionalized NHCs on Au particles. (Wu et al. (2017) Nature 541(7638):511-515).

(FIG. 5C) AFM topographic image of a string of intact exosomes using a platinum-silicate composite tip, (FIG. 5D) same region as shown in C demonstrating superimposed infrared light absorption (dark) within intact exosomes and no surrounding IR-active contaminants, (FIG. 5E) AFM topographic image of a group of individual exosomes using a gold-chromium composite tip, (FIG. 5F) single SINS spectra of the exosome marked by an arrow in the image shown in FIG. 5E (bottom) and the corresponding second derivative, indicating peak positions (top). The raw spectrum is indicated in grey, the processed spectrum in red. The normal amide 1, amide II, non-peptide carbonyl, and other peaks associated with oxidative damage are labeled, (FIG. 5G) diagram of the height (y-axis) of individual exosomes along the white line (x-axis) through three individual exosomes shown in the lower right hand corner of the image shown in FIG. 5E.

DETAILED DESCRIPTION OF EMBODIMENTS

Figure 1:
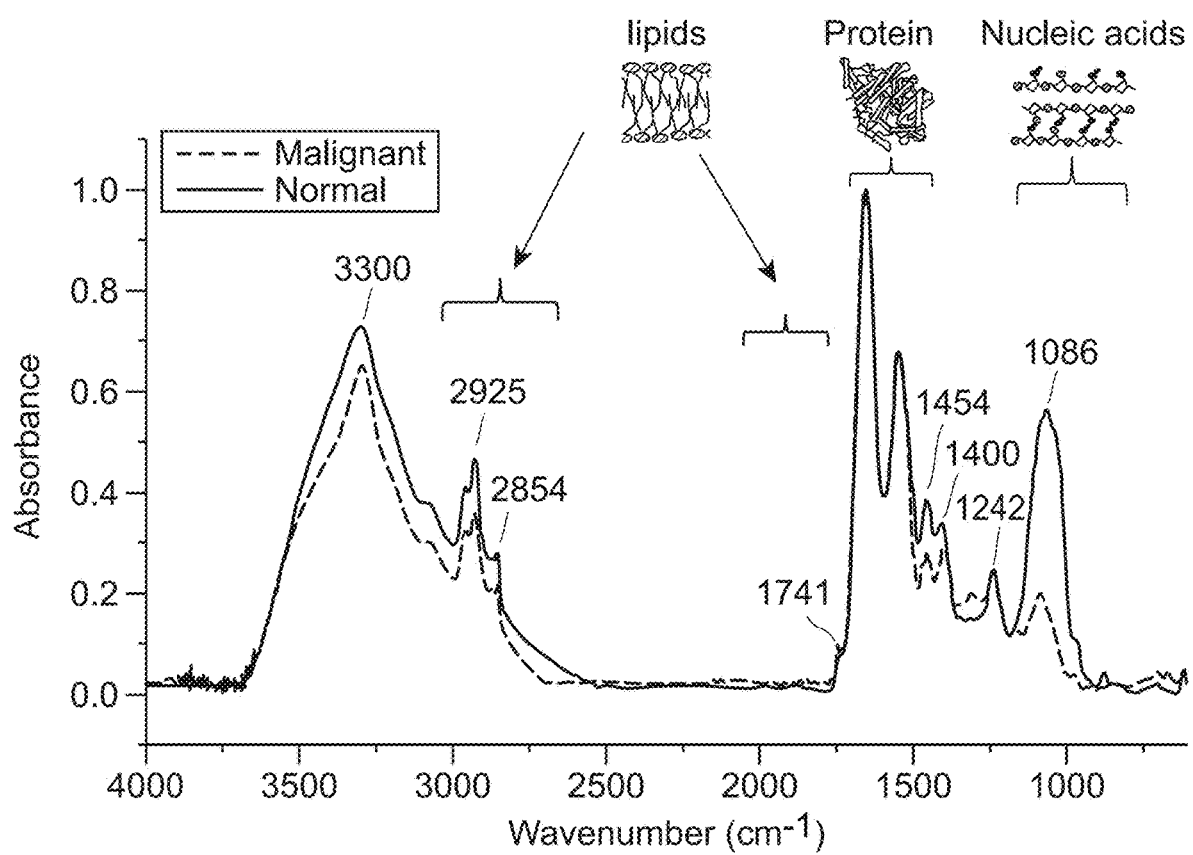
FIG. 1 shows representative FTIR spectra of normal and malignant ovarian tissue. FTIR spectromicroscopy identifies clear differences between normal (blue) and malignant (red) ovarian tissue. Band signals of interest are as follows. 1) Amide A, 3300 cm$^{-1}$. 2) Alkyl chain (primarily lipid)-associated CH2/CH3 symmetric and antisymmetric stretching, 2800-3000 cm$^{-1}$. 3) Ester (C=O) stretching associated with phospholipids, 1741 cm$^{-1}$. 4) Protein amide 1 (C=O stretching) and amide II (N—H bending plus C—N stretching), 1540-1680 cm$^{-1}$. 5) C—H bending associated with proteins and some lipids, 1454 and 1400 cm$^{-1}$. 6) Nucleic acid-associated $PO_2$—symmetric and antisymmetric stretching, 1242 and 1086 cm$^{-1}$.
Figure 2:
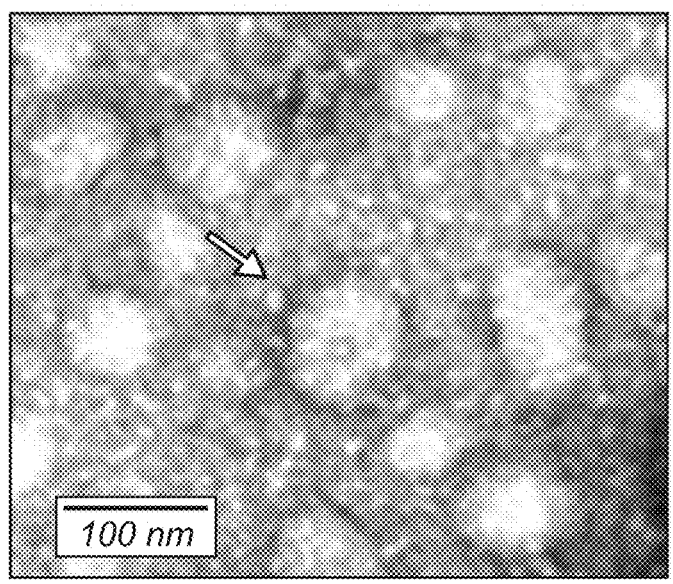
FIG. 2 shows a representative electron micrograph of exosomes isolated from an invasive ovarian cancer cell line SKOV-3.

Methods of detecting diagnostic biomarkers on cancer-derived extracellular vesicles such as exosomes by mid-infrared spectroscopy are provided. In particular, methods of detecting ovarian cancer by spectral fingerprint analysis of molecular vibrational spectroscopic markers on extracellular vesicles (e.g., exosomes) are disclosed.

Before the present diagnostic methods are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "an exosome" includes a plurality of such exosomes and reference to "the extracellular vesicle" includes reference to one or more extracellular vesicles and equivalents thereof, e.g., exosomes, ectosomes, microparticles, microvesicles, or nanosomes, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. The terms "polypeptide" and "protein" refer to a polymer of amino acid residues and are not limited to a minimum length. Thus, peptides, oligopeptides, dimers, multimers, and the like, are included within the definition. Both full-length proteins and fragments thereof are encompassed by the definition. The terms also include postexpression modifications of the protein, for example, glycosylation, acetylation, phosphorylation, hydroxylation, oxidation, and the like.

Biological sample. The term "sample" with respect to an individual encompasses any sample comprising extracellular vesicles (e.g., exosomes) such as blood and other liquid samples of biological origin, solid tissue samples such as a biopsy specimen or cancerous tissue from a surgically resected tumor, malignant effusion fluid samples, or tissue cultures or cells derived or isolated therefrom, and the progeny thereof. The definition also includes samples that have been manipulated in any way after their procurement, such as by treatment with reagents; washed; or enrichment for certain vesicle populations, such as cancer-derived vesicles. The definition also includes samples that have been enriched for particular types of molecules, e.g., lipids, nucleic acids, polypeptides, etc.

The term "biological sample" encompasses a clinical sample. The types of "biological samples" include but are not limited to: tissue obtained by surgical resection, tissue obtained by biopsy, cells in culture, cell supernatants, cell lysates, tissue samples, organs, bone marrow, blood, plasma, serum, urine, amniotic fluid, malignant ascites fluid, cerebral spinal fluid, fine needle aspirate, lymph node aspirate, cystic aspirate, a paracentesis sample, a thoracentesis sample, and the like.

The terms "obtained" or "obtaining" as used herein can also include the physical extraction or isolation of a biological sample (e.g., comprising extracellular vesicles) from a subject. Accordingly, a biological sample can be isolated from a subject (and thus "obtained") by the same person or same entity that subsequently performs diagnostic assays on the racellular vesicles in the sample. When a biological sample is "extracted" or "isolated" from a first party or entity and then transferred (e.g., delivered, mailed, etc.) to a second party, the sample was "obtained" by the first party (and also "isolated" by the first party), and then subsequently "obtained" (but not "isolated") by the second party. Accordingly, in some embodiments, the step of obtaining does not comprise the step of isolating a biological sample.

In some embodiments, the step of obtaining comprises the step of isolating a biological sample (e.g., a pre-treatment biological sample, a post-treatment biological sample, etc.). Methods and protocols for isolating various biological samples (e.g., a blood sample, a serum sample, a plasma sample, a biopsy sample, an aspirate, etc.) will be known to one of ordinary skill in the art and any convenient method may be used to isolate a biological sample.

The phrase "differentially expressed" refers to differences in the quantity and/or the frequency of a biomarker present on extracellular vesicles in a biological sample (e.g., blood) taken from patients having, for example, ovarian cancer as compared to control subjects. For example, a biomarker can be a protein or lipid, which is present at an elevated level or at a decreased level on extracellular vesicles in samples from patients with ovarian cancer compared to samples from control subjects. Alternatively, a biomarker can be a protein or a lipid, which is detected at a higher frequency or at a lower frequency on extracellular vesicles in samples from patients with ovarian cancer compared to samples from control subjects or control tissues. A biomarker can be differentially present in terms of quantity, frequency or both.

A protein or lipid is differentially present between two samples if the amount of the protein or lipid in extracellular vesicles in one sample is statistically significantly different from the amount of the protein or lipid in extracellular vesicles in the other sample. For example, a protein or lipid is differentially present in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

A "diagnostic amount" of a biomarker refers to an amount of a biomarker in a subject's sample that is consistent with a diagnosis of cancer. A diagnostic amount can be either an absolute amount (e.g., µg/ml) or a relative amount (e.g., relative intensity of signals or peak area ratios). Quantification may be determined, for example, from peak area ratios, absolute intensities, or peak areas in an infrared spectrum.

A "control amount" of a biomarker can be any amount or a range of amount which is to be compared against a test amount of a biomarker. For example, a control amount of a biomarker can be the amount of a biomarker in a person without cancer, or normal tissue or cells, or untreated tissue or cells. A control amount can be either an absolute amount (e.g., µg/ml) or a relative amount (e.g., relative intensity of signals or peak area ratios). Quantification may be determined, for example, from peak area ratios, absolute intensities, or peak areas in an infrared spectrum.

Alternatively or additionally, a protein or lipid is differentially present in two sets of samples if the frequency of detecting the protein or lipid in extracellular vesicles in samples of ovarian cancer patients is statistically significantly higher or lower than in samples of control subjects. For example, a protein is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239: 1534-1536; and U.K. Patent Publication No. GB 2,276,169, published 21 Sep. 1994); and, any functional fragments obtained from such molecules, wherein such fragments retain specific-binding properties of the parent antibody molecule.

"Immunoassay" is an assay that uses an antibody to specifically bind an antigen (e.g., a marker). The immunoassay is characterized by the use of specific binding properties of a particular antibody to isolate, target, and/or quantify the antigen. An immunoassay for a protein marker may utilize one antibody or several antibodies. Immunoassay protocols may be based, for example, upon competition, direct reaction, or sandwich type assays using, for example, a labeled antibody. The labels may be, for example, fluorescent, chemiluminescent, or radioactive.

The phrase "specifically (or selectively) binds" to an antibody or "specifically (or selectively) immunoreactive with," when referring to a protein or peptide, refers to a binding reaction that is determinative of the presence of the protein marker in a heterogeneous population of proteins and other biologics. Thus, under designated immunoassay conditions, the specified antibodies bind to a particular protein marker at least two times the background and do not substantially bind in a significant amount to other proteins present in the sample. Specific binding to an antibody under such conditions may require an antibody that is selected for its specificity for a particular protein marker. For example, polyclonal antibodies raised to a protein marker from specific species such as rat, mouse, or human can be selected to obtain only those polyclonal antibodies that are specifically immunoreactive with the protein marker and not with other proteins, except for polymorphic variants and alleles of the protein marker. This selection may be achieved by subtracting out antibodies that cross-react with biomarker molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane. Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

"Capture reagent" refers to a molecule or group of molecules that specifically bind to a specific target molecule or group of target molecules. For example, a capture reagent can comprise two or more antibodies each antibody having specificity for a separate target molecule. Capture reagents can be any combination of organic or inorganic chemicals, or biomolecules, and all fragments, analogs, homologs, conjugates, and derivatives thereof that can specifically bind a target molecule.

The capture reagent can comprise a single molecule that can form a complex with multiple targets, for example, a multimeric fusion protein with multiple binding sites for different targets. The capture reagent can comprise multiple molecules each having specificity for a different target, thereby resulting in multiple capture reagent-target complexes. In certain embodiments, the capture reagent is comprised of proteins, such as antibodies.

The capture reagent can be directly labeled with a detectable moiety. For example, an anti-marker antibody can be directly conjugated to a detectable moiety and used in the inventive methods, devices, and kits. In the alternative, detection of the capture reagent-marker complex can be by a secondary reagent that specifically binds to the marker or the capture reagent-marker complex. The secondary reagent can be any biomolecule, and is preferably an antibody. The secondary reagent is labeled with a detectable moiety. In some embodiments, the capture reagent or secondary reagent is coupled to biotin, and contacted with avidin or streptavidin having a detectable moiety tag.

"Detectable moieties" or "detectable labels" contemplated for use in the methods described herein include, but are not limited to, radioisotopes such as such as $^3H$, $^{14}C$, $^{32}P$, and $^{125}I$; metal isotopes such as rare earth elements, including cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) and yttrium (Y); fluorescent dyes such as SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, rhodamine, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), carboxy-X-rhodamine (ROX), tetramethyl rhodamine (TAMRA), FITC, dansyl, umbelliferone, dimethyl acridinium ester (DMAE), Texas red, luminol, and quantum dots, enzymes such as alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), (β-galactosidase (lacZ), and xanthine guanine phosphoribosyltransferase (XGPRT), beta-glucuronidase (gus), placental alkaline phosphatase (PLAP), and secreted embryonic alkaline phosphatase (SEAP). Enzyme tags are used with their cognate substrate. The terms also include chemiluminescent labels such as luminol, isoluminol, acridinium esters, and peroxyoxalate and bioluminescent proteins such as firefly luciferase, bacterial luciferase, Renilla luciferase, and aequorin. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

"Diagnosis" as used herein generally includes determination as to whether a subject is likely affected by a given disease, disorder or dysfunction. The skilled artisan often makes a diagnosis on the basis of one or more diagnostic indicators, i.e., a marker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer) as well as those in which prevention is desired (e.g., those with increased susceptibility to cancer, those suspected of having cancer, those with a genetic predisposition to developing cancer, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, or IV) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, neuroendocrine carcinoma, and small cell carcinoma. These terms include, but are not limited to, ovarian cancer, breast cancer, prostate cancer, lung cancer, testicular cancer, colon cancer, rectal cancer, pancreatic cancer, gastrointestinal cancer, hepatic cancer, endometrial cancer, leukemia, lymphoma, adrenal cancer, thyroid cancer, pituitary cancer, adrenocortical cancer, renal cancer, brain cancer (e.g., glioblastoma and astrocytoma), skin cancer (e.g., basal-cell cancer, squamous-cell cancer, and melanoma), head cancer, neck cancer, oral cavity cancer, tongue cancer, and esophageal cancer.

For example, the term "ovarian cancer" includes any type of ovarian cancer at any stage (e.g., I-IV), including, without limitation, ovarian epithelial carcinoma, low-grade serous carcinoma, high-grade serous carcinoma, small-cell ovarian carcinoma, primary peritoneal carcinoma, clear-cell adenocarcinoma, endometrioid adenocarcinoma, mixed müllerian carcinosarcoma, mucinous adenocarcinoma, mucinous cystadenocarcinoma, pseudomyxoma peritonei, undifferentiated epithelial ovarian cancer, malignant Brenner tumors, transitional cell carcinoma, granulosa cell tumors, dysgerminoma, choriocarcinoma, and ovarian squamous cell carcinoma.

"Substantially purified" generally refers to isolation of a substance (compound, drug, polynucleotide, protein, polypeptide) such that the substance comprises the majority percent of the sample in which it resides. Typically in a sample, a substantially purified component comprises 50%, preferably 80%-85%, more preferably 90-95% of the sample. Techniques for purifying substances of interest are well-known in the art and include, for example, ion-exchange chromatography, affinity chromatography and sedimentation according to density.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

Methods

Efficient methods for detecting biomarkers on extracellular vesicles using mid-infrared vibrational spectroscopy are disclosed. The methods described herein can be applied to extracellular vesicles including, but not limited to, exosomes, ectosomes, microparticles, microvesicles, and nanosomes. In particular the methods described herein are useful for diagnosing cancer based on analysis of spectral chemical fingerprints of biomarkers from extracellular vesicles (e.g., exosomes) derived from cancerous cells.

Biomarkers on Extracellular Vesicles for Diagnosing Cancer

Mid-infrared vibrational spectroscopy can be used to detect biomarkers associated with tumor-derived extracellular vesicles to allow rapid clinical screening of cancer. Extracellular vesicles comprise a portion of the cellular contents and lipid bilayer from the parent cell from which they originated and therefore share biomarkers in common with their parent cell. The biomarkers described herein are associated with extracellular vesicles (e.g., exosomes) derived from ovarian cancer cells, and accordingly, are useful in diagnosing cancer, particularly ovarian cancer.

In some embodiments, the biomarkers are lipids or membrane-bound or adsorbed proteins on the extracellular vesicles. In some embodiments, the one or more biomarkers are cancer cell-specific proteins. In some embodiments, at least one biomarker is an exosome surface marker. In one embodiment, at least one biomarker is phosphatidylserine. The membrane-bound or adsorbed biomarkers on the extracellular vesicles can be detected without lysis or permeabilization of the vesicles.

A biological sample comprising extracellular vesicles (e.g., exosomes) may be obtained from a subject. The biological sample obtained from the subject is typically blood, but can be any sample from bodily fluids, tissue or cells comprising the extracellular vesicles to be analyzed. The biological sample may include, but is not limited to, whole blood, serum, plasma, urine, amniotic fluid, malignant ascites fluid, interstitial fluid, peritoneal fluid, cerebrospinal fluid, a cervical swab, tears, saliva, a buccal swab, skin, organs, and biopsies (e.g., tumor biopsy). For example, the biological sample may comprise extracellular vesicles such as exosomes from ovarian cancer cells from a tumor. Alternatively, extracellular vesicles can be obtained from cultured cells by collection of secreted vesicles from the surrounding culture media.

In some embodiments, the biological sample comprising extracellular vesicles is obtained from blood. In some embodiments, about 1-10 mL of blood is drawn from a subject. In other embodiments, about 10-50 mL of blood is drawn from a subject. Blood can be drawn from any suitable area of the body, including an arm, a leg, or blood accessible through a central venous catheter. In some embodiments, blood is collected following a treatment or activity. For example, blood can be collected following a medical exam. The timing of collection can also be coordinated to increase the number and/or composition of vesicles (e.g., exosomes) present in the sample. For example, blood can be collected following exercise or a treatment that induces vascular dilation.

Blood may be combined with various components following collection to preserve or prepare samples for subsequent analysis. For example, in some embodiments, blood is treated with an anticoagulant, a cell fixative, a protease inhibitor, a phosphatase inhibitor, a protein, a DNA, or an RNA preservative following collection. In some embodiments, blood is collected via venipuncture using vacuum collection tubes containing an anticoagulant such as EDTA or heparin. Blood can also be collected using a heparin-coated syringe and hypodermic needle. Blood can also be combined with components that will be useful for cell culture. For example, in some embodiments, blood is combined with cell culture media or supplemented cell culture media. In one embodiment, the culture media is supplemented with annexin V.

When analyzing the biomarkers of extracellular vesicles, a mid-infrared spectrum of one or more extracellular vesicles from a biological sample from a patient is obtained and may be compared to one or more reference spectra of one or more extracellular vesicles from one or more control samples. A "control" sample, as used herein, refers to a sample comprising extracellular vesicles that are derived from an individual who is not diseased. That is, a control sample is obtained from a normal subject (e.g. an individual known to not have cancer or any condition or symptom associated with abnormal cell maturation or proliferation). Alternatively, the mid-infrared spectrum of one or more extracellular vesicles from a biological sample from a patient may be compared to one or more reference spectra of one or more cancer-derived extracellular vesicles from samples from one or more patients who have cancer. More specifically, the reference spectra may be of one or more cancer-derived extracellular vesicles from samples of one or more patients having cancer at a particular stage. For example, in some embodiments, the cancer is ovarian cancer, and the mid-infrared spectrum of the cancer-derived extracellular vesicles from the biological sample of the patient may be compared to the mid-infrared spectrum of cancer-derived extracellular vesicles from a reference sample obtained from a subject with early stage ovarian cancer (i.e., at stage I or stage II) or late stage ovarian cancer (i.e., at stage III or stage IV) to provide an estimation of the cancer stage of the patient.

In some embodiments, a panel of biomarkers are used for diagnosing cancer (e.g., ovarian cancer). Such a panel may comprise 1, 2, 3, 4, 5, 6, 7, 8, 9, 10, 15, 20, or more or individual biomarkers from extracellular vesicles. The analysis of a single biomarker or subsets of biomarkers on extracellular vesicles in a larger panel of biomarkers, or an entire biomarker panel can be carried out to optimize clinical sensitivity or specificity in various clinical settings.

Detecting Vesicular Biomarkers by Mid-Infrared Vibrational Spectroscopy

The biomarkers from cancer-derived extracellular vesicles in a sample can be detected by mid-Infrared vibrational spectroscopy. Mid-infrared vibrational spectroscopy utilizes electromagnetic radiation in the range from approximately 4000 to 400 $cm^{-1}$ (2.5-25 µm), which excites molecular vibrations to higher energy levels. The wavelength of infrared absorption bands are characteristic of specific types of chemical bonds. Absorption bands for lipids (about 2800 $cm^{-1}$ to about 3000 $cm^{-1}$), proteins (about 1500 $cm^{-1}$ to about 1700 $cm^{-1}$), and polysaccharides (about 900 $cm^{-1}$ to about 1300 $cm^{-1}$) can provide a characteristic "fingerprint" or signature for an extracellular vesicle that reflects pathological changes. That is, mid-Infrared spectra can provide molecular fingerprints based on the characteristic vibrational frequencies of particular chemical bonds and chemical functional groups belonging to the biomarkers on extracellular vesicles, which are capable of differentiating between vesicles that originated from normal cells (i.e., having a "normal" spectral chemical fingerprint) versus malignant tissue or cancerous cells (i.e., having a "diseased" or "cancerous" spectral chemical fingerprint).

Instruments for measuring infrared absorption utilize a source of infrared radiation and a sensitive infrared detector. Conventional infrared light sources consist of an inert solid that is electrically heated to a temperature between 1,500 and 2,200 K causing the solid to emit infrared radiation. Exemplary sources of infrared radiation include a Nernst glower (hollow cylinder composed of rare earth oxides) and a globar source (rod of silicon carbide). Alternatively, a tuneable carbon dioxide laser, a quantum cascade laser-based device, or a synchrotron source may be used. The choice of light source depends on the application, the desired sensitivity of detection, time required for spectral acquisition, the number of species being detected, the resolution needed for discrimination between similar species, and the like. Depending on the application, either a narrow-band (e.g., quantum cascade laser) or broadband (e.g., synchrotron) mid-infrared light source may be used. Exemplary infrared detectors include thermal detectors, pyroelectric detectors and photoconducting detectors.

In some embodiments, synchrotron infrared nanospectroscopy (SINS) is used to record a spectrum. SINS can provide nanoscale images of extracellular vesicles. The synchrotron beam is focused onto an atomic force microscope (AFM) probe such that the optical field is spatially constrained to the surface of the AFM probe tip. The optical resolution is typically about 25 nm. Other AFM-coupled IR technologies may also be used. For example, an AFM probe may be used with a pulsed laser or other infrared source. SINS-AFM-FTIR and other AFM-coupled IR technologies can be used to detect individual cancer-derived extracellular vesicles in a sample using broadband mid-infrared radiation from synchrotron or laser sources. For a description of SINS-AFM-FTIR and other AFM-coupled IR technologies, see, e.g., Freitas et al. (2018) Optics Express 26:11238-11249, Bechtel et al. (2014) Proc. Natl. Acad. Sci. U.S.A. 111(20):7191-7196, Dazzi et al. (2005) Optics Letters. 30 (18): 2388-2390, Dazzi et al. (2012) Applied Spectroscopy. 66 (12): 1365-1384, Hill et al. (2009) Optics Letters. 34 (4):433; herein incorporated by reference.

In some embodiments, infrared spectroscopy is performed with a diffraction-limited laser beam, which can be focused on a single cancer-derived extracellular vesicle to provide images of individual vesicles. The diffraction-limited laser can be used in combination with a microfluidic device for high-throughput analysis of extracellular vesicles. For example, the diffraction-limited laser beam can be focused on a single cancer-derived extracellular vesicle in a microfluidic channel or chamber of the microfluidic device.

Spectra can be recorded of a population of extracellular vesicles or a single extracellular vesicle by exposing the extracellular vesicles to mid-infrared light. In some embodiments, spectra of extracellular vesicles are compared to a reference spectrum. For example, a spectrum of a cancer-derived extracellular vesicle from a patient can be compared to a reference spectrum of a "control" extracellular vesicle derived from an individual who is not diseased (i.e., normal subject known to not have cancer) or a noncancerous extracellular vesicle from the patient. Alternatively, a spectrum of an extracellular vesicle from a patient can be compared to one or more reference spectra of cancer-derived extracellular vesicles from individuals who have cancer. In some embodiments, the reference spectra are of extracellular vesicles from individuals at different cancer stages. For example, for a patient who has ovarian cancer, a spectrum of a cancer-derived extracellular vesicle from the patient can be compared to one or more reference spectra of cancer-derived extracellular vesicles from individuals having early stage ovarian cancer (i.e., at stage I or stage II) or late stage ovarian cancer (i.e., at stage III or stage IV) to allow an estimate of the cancer stage of the patient.

In certain embodiments, cancer risk is determined by detection of individual cancer-derived extracellular vesicles. Bulk sampling methods which average signal over the whole sample population are much less effective in evaluating cancer risk. In certain embodiments, the cancer-derived extracellular vesicles are dispersed to allow imaging of individual exosomes and subpopulations of exosomes in a sample. The cancer-derived extracellular vesicles in the sample can be sufficiently dispersed to allow imaging of a single cancer-derived extracellular vesicle. Exosomes can be dispersed, for example, in the presence of annexin V and $Ca^{2+}$ (e.g., $CaCl_2$) or $Ca^{2+}$ without annexin V for single-exosome imaging (see Example 1).

In certain embodiments, the biomarker, phosphatidylserine, is detected in cancer-derived extracellular vesicles, wherein detection of an increased level of the phosphatidylserine in the cancer-derived extracellular vesicle membrane compared to a control level of the phosphatidylserine indicates that the patient has cancer. Phosphatidylserine can be detected with a phosphatidylserine binding agent. Binding of the agent to phosphatidylserine may cause local increases in membrane stiffness and bilayer deformation, which are detectable by mid-infrared spectroscopy. Exemplary phosphatidylserine binding agents include, without limitation, proteins, peptides, antibodies, aptamers, and small molecules that bind selectively to phosphatidylserine. A variety of phosphatidylserine binding agents are known in the art and can be used in detecting phosphatidylserine, including, without limitation, annexin V and other phosphatidylserine-binding proteins and peptides (see, e.g., van Genderen et al. (2008) Biochim Biophys Acta 1783(6):953-963, van Engeland et al. (1998) Cytometry 31(1):1-9, Stace et al. (2006) Biochim Biophys Acta 1761(8): 913-926, Burtea et al. (2009) Mol. Pharm. 6(6):1903-1919, Igarashi et al (1995) J. Biol. Chem. 270(49):29075-29078, Laumonier et al. (2006) J. Biomol. Screen. 11(5):537-545, and Thapa et al (2008) J. Cell. Mol. Med 0.12(5A):1649-1660; herein incorporated by reference), small molecules including annexin mimics (e.g., $Zn^{2+}$-2,20-dipicolylamine ($Zn^{2+}$-DPA also referred to as PSS-380) described by Hanshaw et al. (2005) Bioorg. Med. Chem 13(17):5035-5042, herein incorporated by reference), phosphatidylserine-binding aptamers (see, e.g., Ashrafuzzaman et al. (2013) Nucleic Acid Ther. 23(6):418-426, herein incorporated by reference), and antibodies specific for phosphatidylserine (see, e.g., Ran et al. (2005) Clin. Cancer Res. 11(4):1551-1562, He et al. (2009) Clin Cancer Res. 2009; 15(22):6871-6880; herein incorporated by reference).

The identified biomarkers from extracellular vesicles serve an important role in the early detection and monitoring of cancer (e.g., ovarian cancer). The detection of a biomarker on extracellular vesicles correlates with disease pathophysiology, the presence or absence of cancer, the probability of developing cancer, or cancer recurrence. In patients receiving treatment for their condition the detection of biomarkers associated with extracellular vesicles will also correlate with responsiveness to therapy. In some embodiments, a decrease or increase in the amount of extracellular vesicles having one or more biomarkers indicative of cancer may be an indication of disease severity. For example, detection of an increase in levels of phosphatidylserine in the membranes of exosomes and/or an increase in the number of exosomes having increased levels of phosphatidylserine is indicative of ovarian cancer. Accordingly, the methods described herein are useful for the detection of ovarian cancer.

In addition, medical imaging of a patient can be used to confirm a diagnosis of cancer and locate the cancer if extracellular vesicles from the patient have a mid-infrared spectral chemical fingerprint indicating that the patient is at risk of having cancer. Exemplary medical imaging techniques include, without limitation, radiography, magnetic resonance imaging (MRI), ultrasound, photoacoustic imaging, computed tomography (CT), positron emission tomography (PET), single-photon emission computed tomography (SPECT), endoscopy, optical imaging, fluorescence imaging, elastography, and thermography. A patient diagnosed as being at risk of cancer based on the mid-infrared spectral chemical fingerprint of a cancer-derived extracellular vesicle may also further undergo a biopsy, laparoscopy, or surgical resection of the cancer. Patients with a confirmed positive diagnosis for cancer should be administered a suitable anti-cancer therapy such as, for example, including without limitation, surgery, radiation therapy, chemotherapy, targeted therapy, anti-angiogenic therapy, or immunotherapy, or any combination thereof.

Isolation and Detection of Extracellular Vesicles

In some embodiments, extracellular vesicles are isolated from samples prior to performing infrared spectroscopy. Extracellular vesicles are typically isolated from biological samples (e.g. blood or plasma) by ultracentrifugation and precipitation by well-known methods. Biological samples can be centrifuged to remove cells and larger cellular debris followed by ultracentrifugation to isolate extracellular vesicles as a pellet. For example, differential centrifugation with sequentially increasing centrifugal force allows the removal of cells, cellular debris, larger particles and organelles from the sample (e.g., bodily fluid such as blood or plasma or conditioned cell culture supernatant comprising extracellular vesicles) and collection of the extracellular vesicles. A density gradient may also be applied for sample separation. Ultrafiltration and/or size-exclusion chromatography can be used to remove contaminating components from the sample. In addition, liquid chromatography (e.g.

ultra or high-performance liquid chromatography (UPLC or HPLC), immunoaffinity capture methods, and/or electrophoresis (e.g., capillary electrophoresis) can be used to further purify extracellular vesicles. In some embodiments, the extracellular vesicles are substantially purified prior to imaging. For a description of various methods of isolating extracellular vesicles, see, e.g., Menck et al. (2017) J Vis Exp. (119); Xu et al. (2015) Methods 87:11-25; Tauro et al. (2012) Methods 56(2):293-304; Muller et al. (2014) J. Immunol. Methods 411:55-65; herein incorporated by reference.

Samples can be further enriched for extracellular vesicles of interest (i.e., cancer-derived vesicles comprising at least one ovarian cancer biomarker) by any suitable method known in the art. The extracellular vesicles enriched in the biological samples may include, but are not limited to, exosomes, microparticles, microvesicles, nanosomes, and ectosomes. In some embodiments, the extracellular vesicles enriched in the biological samples are cancer-derived exosomes. In some embodiments, samples are enriched for extracellular vesicles through positive selection, negative selection, or a combination thereof. In positive selection, extracellular vesicles carrying a selection marker are collected, whereas in negative selection, extracellular vesicles carrying a selection marker are removed from a vesicle population. For example, in positive selection, a capture agent specific for a surface marker on an extracellular vesicle can be immobilized on a solid support (e.g., column or magnetic bead) and used to collect extracellular vesicles having the surface marker on the solid support. Extracellular vesicles that are not of interest do not bind to the solid support (e.g., flow through the column or do not attach to the magnetic beads). In negative selection, the capture agent is used to deplete a sample of extracellular vesicles and other material (e.g., cells, cellular debris, and other material) that are not of interest. The extracellular vesicles of interest are those that do not bind to the capture agent (e.g., flow through the column or remain after the magnetic beads are removed). In some embodiments, extracellular vesicles are directly captured by a capture agent using positive selection. In other embodiments, blood cells from a blood sample are captured to deplete the sample of blood cells, and extracellular vesicles are subsequently collected from the remaining portion of the sample.

In some embodiments, enriched extracellular vesicles from a biological sample are subsequently enriched for a specific type of extracellular vesicle. For example, the biological sample can be enriched for exosomes and then subsequently enriched for cancer-derived exosomes. In some embodiments, the biological sample is enriched for extracellular vesicles derived from a particular source such as exosomes derived from an ovarian tumor. In some embodiments, a capture agent is used that selectively binds to an exosome surface marker (e.g., CD81) to capture exosomes generally, and a cancer-specific marker (e.g., phosphatidylserine) is used to capture cancer-derived exosomes.

In some embodiments, extracellular vesicles are isolated or enriched from a biological sample by contacting a biological sample with a capture agent under conditions wherein an extracellular vesicle present in the biological sample binds to the capture agent to form a vesicle-capture agent complex; and the extracellular vesicle is isolated from the vesicle-capture agent complex to obtain a sample of purified extracellular vesicles, wherein the purity of the extracellular vesicles present in the sample is greater than the purity of the extracellular vesicles present in the original biological sample. In some embodiments, multiple isolating or enriching steps are performed. For example, a first isolating step may be performed to isolate exosomes from a blood sample followed by a second isolating step to isolate cancer-derived exosomes (e.g., ovarian cancer-derived exosomes) from other exosomes.

In yet other embodiments, the methods further comprise releasing the extracellular vesicle from the vesicle-capture agent complex. For example, the vesicle can be released by exposing the vesicle-agent complex to low pH between 3.5 and 1.5. The composition comprising the released vesicle may subsequently be neutralized by adding a high pH solution. Alternatively, the vesicle can be released using a competing peptide that competes with the capture agent for the binding of markers on the extracellular vesicle. In some embodiments, the extracellular vesicle is lysed (either while in the vesicle-capture agent complex or after release) by incubating the extracellular vesicle with a lysis solution. The lysis solution may contain inhibitors for proteases or phosphatases.

In some embodiments, a subset of the extracellular vesicles is separated from other vesicles in a biological sample using capture agents immobilized on a solid support. Such capture agents bind selectively to a surface marker (e.g., lipid, membrane protein or adsorbed protein) on the extracellular vesicles such that the capture agent can "capture" extracellular vesicles having the surface marker. By "capture" is meant that the target extracellular vesicle can be separated from other vesicles in the sample by virtue of the binding of the capture agent to the surface marker on the extracellular vesicle.

The specificity of the capture agent determines the subset of extracellular vesicles from a biological sample that are captured on the solid support. One or more capture agents can be used in combination in order to capture extracellular vesicles having different surface markers. For example, the solid support may comprise more than one type of capture agent associated therewith, for example, at least 2, 3, 4, 5, 6, 7, 8, 9, 10, 15, 20, or more different capture agents that selectively bind to different biomarkers on the extracellular vesicles. In some embodiments, the extracellular vesicles targeted by a capture agent are exosomes, microparticles, microvesicles, nanosomes, or ectosomes.

Typically, the capture agent is associated with a solid support, either directly or indirectly. Capture agents may be immobilized on the surface of a solid support, such as, but not limited to, a plate, slide, wafer, non-magnetic bead, magnetic bead, rod, particle, strand, disc, membrane, film, or the inner surface of a tube, channel, column, flow cell device, or microfluidic device. A solid support may comprise various materials, including, but not limited to glass, quartz, silicon, metal, ceramic, plastic, nylon, polyacrylamide, agarose, resin, porous polymer monoliths, hydrogels, and composites thereof. Additionally, a substrate may be added to the surface of a solid support to facilitate attachment of a capture agent.

Once captured on the solid support, the extracellular vesicles can be screened for one or more lipids or membrane-bound or adsorbed proteins using detection agents without the need for lysis or permeabilization of the vesicles. Such detection agents bind selectively to membrane-bound or adsorbed biomarkers on the vesicles. In certain embodiments, the detection agent (e.g. annexin V) selectively binds to a cancer biomarker (e.g., phosphatidylserine). In certain embodiments, detection of biomarkers on extracellular vesicles captured on the solid support comprises using more than one type of detection agent, for example, at least 2, 3, 4, 5, 6, 7, 8, 9, 10, 15, 20, or more different detection agents that selectively bind to different biomarkers on the vesicles.

Capture agents and detection agents may comprise, for example, including, without limitation, proteins, peptides, antibodies, antibody fragments, antibody mimetics, or aptamers that specifically bind to a biomarker (e.g., lipid or membrane-bound or adsorbed protein) on a vesicle. The phrase "specifically (or selectively) binds" refers to a binding reaction that is determinative of the presence of the biomarker on an extracellular vesicle in a heterogeneous population of cells, vesicles, proteins and other biologics. Thus, under designated assay conditions, the specified capture agents or detection agents bind to a particular biomarker on an extracellular vesicle at least two times the background and do not substantially bind in a significant amount to other proteins present in the sample. In some embodiments, the capture agent binds to the biomarker with high affinity. The capture agent may be immobilized on a solid support to facilitate isolation of extracellular vesicles of interest from a liquid culture. Exemplary solid supports include a magnetic bead, a non-magnetic bead, a slide, a gel, a membrane, and a microtiter plate well.

In certain embodiments, the capture agent or detection agent comprises an antibody that specifically binds to a surface marker (e.g., membrane protein or adsorbed protein) on a vesicle. Any type of antibody may be used, including polyclonal and monoclonal antibodies, hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule (i.e., specifically binds to a target surface marker on a vesicle).

In other embodiments, the capture agent or detection agent comprises an aptamer that specifically binds to the target biomarker on an extracellular vesicle. Any type of aptamer may be used, including a DNA, RNA, xeno-nucleic acid (XNA), or peptide aptamer that specifically binds to the target antibody isotype. Such aptamers can be identified, for example, by screening a combinatorial library. Nucleic acid aptamers (e.g., DNA or RNA aptamers) that bind selectively to a target antibody isotype can be produced by carrying out repeated rounds of in vitro selection or systematic evolution of ligands by exponential enrichment (SELEX). Peptide aptamers that bind to a target antibody isotype may be isolated from a combinatorial library and improved by directed mutation or repeated rounds of mutagenesis and selection. For a description of methods of producing aptamers, see, e.g., *Aptamers: Tools for Nanotherapy and Molecular Imaging* (R. N. Veedu ed., Pan Stanford, 2016), *Nucleic Acid and Peptide Aptamers: Methods and Protocols* (Methods in Molecular Biology, G. Mayer ed., Humana Press, 2009), Nucleic Acid Aptamers: *Selection, Characterization, and Application* (Methods in Molecular Biology, G. Mayer ed., Humana Press, 2016), *Aptamers Selected by Cell-SELEX for Theranostics* (W. Tan, X. Fang eds., Springer, 2015), Cox et al. (2001) Bioorg. Med. Chem. 9(10):2525-2531; Cox et al. (2002) Nucleic Acids Res. 30(20): e108, Kenan et al. (1999) Methods Mol Biol. 118:217-231; Platella et al. (2016) Biochim. Biophys. Acta Nov 16 pii: S0304-4165(16)30447-0, and Lyu et al. (2016) Theranostics 6(9):1440-1452; herein incorporated by reference in their entireties.

In yet other embodiments, the capture agent or detection agent comprises an antibody mimetic. Any type of antibody mimetic may be used, including, but not limited to, affibody molecules (Nygren (2008) FEBS J. 275 (11):2668-2676), affilins (Ebersbach et al. (2007) J. Mol. Biol. 372 (1):172-185), affimers (Johnson et al. (2012) Anal. Chem. 84 (15): 6553-6560), affitins (Krehenbrink et al. (2008) J. Mol. Biol. 383 (5):1058-1068), alphabodies (Desmet et al. (2014) Nature Communications 5:5237), anticalins (Skerra (2008) FEBS J. 275 (11):2677-2683), avimers (Silverman et al. (2005) Nat. Biotechnol. 23 (12):1556-1561), darpins (Stumpp et al. (2008) Drug Discov. Today 13 (15-16):695-701), fynomers (Grabulovski et al. (2007) J. Biol. Chem. 282 (5):3196-3204), and monobodies (Koide et al. (2007) Methods Mol. Biol. 352:95-109).

In certain embodiments, the extracellular vesicle is glycosylated and comprises glycolipids and/or glycoproteins, wherein the capture agent or detection agent comprises a lectin. In some embodiments, a lectin microarray is used to capture extracellular vesicles. Lectins useful for capturing and/or detecting extracellular vesicles are described in Williams et al. (2018) J. Extracell. Vesicles 7(1):1442985; Samsonov et al. (2016) Prostate 76(1):68-79; Echevarria et al. (2014) Chembiochem. 15(11):1621-6; and U.S. Patent Application Publication No. 2012/0077263; herein incorporated by reference.

Detection agents may further comprise a detectable label to facilitate detection and/or quantitation of biomarkers on vesicles. Detectable labels include fluorescent, chemiluminescent, electrochemiluminescent, or bioluminescent tags, metals, dyes, radionuclides, and the like, attached to the specific binding agent (e.g., antibody, antibody fragment, antibody mimetic, or aptamer that specifically binds to a membrane-bound or adsorbed biomarker on vesicles).

In addition, fluorescence-activated cell sorting (FACS) can be used to sort a heterogeneous mixture of vesicles and cells into separate containers. (See, e.g., *Shapiro Practical Flow Cytometry*, Wiley-Liss, 4$^{th}$ edition, 2003; Loken *Immunofluorescence Techniques in Flow Cytometry and Sorting*, Wiley, 2$^{nd}$ edition, 1990; *Flow Cytometry: Principles and Applications*, (ed. Macey), Humana Press 1$^{st}$ edition, 2007; herein incorporated by reference in their entireties.). Flow cytometry sorting may also be used to enrich for extracellular vesicles (e.g., cancer-derived exosomes) using cell surface markers or intracellular or extracellular markers conjugated to fluorescent labels. Intracellular and extracellular markers may be fluorescently labeled, for example, with nuclear stains or fluorescently labeled antibodies against intracellular or extracellular proteins preferentially expressed in cancer-derived extracellular vesicles. In particular, antibodies against surface antigens that are preferentially expressed on cancer-derived exosomes may be used.

Phosphatidylserine can be detected, for example, by contacting the extracellular vesicles with a fluorescently labeled phosphatidylserine binding agent such as annexin V, which binds to phosphatidylserine in the membranes of cancer-derived extracellular vesicles. Extracellular vesicles having the fluorescently labeled binding agent bound to the phosphatidylserine in their membranes can be isolated by FACS. Alternatively or additionally, the extracellular vesicles having the fluorescently labeled binding agent (e.g., annexin V) bound to the phosphatidylserine in their membranes can be isolated by positive selection using a capture agent that specifically binds to the binding agent (e.g., annexin V).

Data Analysis

In some embodiments, detection of a spectral chemical fingerprint for an extracellular vesicle is automated by using a multivariate classification algorithm. Predictive models and/or algorithms can be provided in a machine readable format and may be used to correlate spectral chemical fingerprints for cancer-derived extracellular vesicles of a patient with a risk of cancer, cancer recurrence, or stage of cancer progression. Generating the predictive model may comprise, for example, the use of an algorithm or classifier.

In some embodiments, a machine learning algorithm is used in generating the predictive model. The machine learning algorithm may comprise a supervised learning algorithm. Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithm may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, temporal difference learning, Q-learning and Learning Automata. Alternatively, the machine learning algorithm may comprise Data Pre-processing.

In certain embodiments, the machine learning algorithms include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naïve Bayes classifier, k-nearest neighbor, high-dimensional discriminant analysis, or Gaussian mixture models. In some instances, the machine learning algorithm comprises Random Forests.

Further Analysis of Biomarkers

An advantage of mid-infrared spectroscopy is that it is generally not destructive to samples, which allows the biomarkers on cancer-derived exosomes to be further analyzed by other methods. The methods of the invention can be combined with any other methods known in the art for detecting, quantitating, isolating, identifying, or otherwise further characterizing biomarkers, for example, including without limitation, flow cytometry, fluorescence-associated cell sorting (FACS), immunohistochemistry, enzyme-linked immunosorbent assay (ELISA), immunofluorescent assay (IFA), immune-polymerase chain reaction assay, electro-chemiluminescence immunoassay (ECLIA), radioimmunoassay (RIA), mass spectrometry, and sequencing.

In some embodiments, biomarker levels on extracellular vesicles are further measured in a biological sample obtained from a subject having or at-risk of having cancer (e.g., ovarian cancer). It is understood that the biomarkers on extracellular vesicles in a sample can be quantitated by any suitable method known in the art. For example, levels of protein biomarkers on extracellular vesicles may be determined using an immunoassay. The presence or amount of a biomarker is generally determined using antibodies specific for each biomarker and detecting specific binding. Any suitable immunoassay may be utilized, for example, an enzyme-linked immunosorbent assay (ELISA), immuno-fluorescent assay (IFA), immune-polymerase chain reaction assay, electro-chemiluminescence immunoassay (ECLIA), radioimmunoassay (RIA), competitive binding assay, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The antibodies specific for the biomarkers on extracellular vesicles may be immobilized on a solid support. For example, the antibodies can be immobilized on a variety of solid supports, such as magnetic or chromatographic matrix particles, the surface of an assay place (such as microtiter wells), pieces of a solid substrate material (such as plastic, nylon, paper), and the like. An assay strip can be prepared by coating with the antibody or a plurality of antibodies in an array on solid support. Such a strip can then be dipped into the test sample to capture vesicles through binding to surface markers, and processed quickly through washes and detection steps with detection reagents, as described above, to generate a measurable signal, such as a colored spot.

The analysis of a plurality of biomarkers may be carried out separately or simultaneously with one test sample. Several markers on extracellular vesicles may be captured and/or detected using a combination of multiple capture agents and/or detection agents in one test for efficient processing of multiple of samples. In addition, one skilled in the art would recognize the value of testing multiple samples (for example, at successive time points) from the same individual. Such testing of serial samples will allow the identification of changes in biomarker levels over time. Increases or decreases in biomarker levels, as well as the absence of changes in the biomarker levels, would provide useful information about the disease status that includes, but is not limited to identifying the approximate time from onset of the event, the presence and amount of salvageable tissue, the appropriateness of drug therapies, the effectiveness of various therapies, identification of the severity of the event, identification of the disease severity, and identification of the patient's outcome, including risk of future events.

The analysis of biomarkers can be carried out in a variety of physical formats as well.

For example, the use of microtiter plates or automation can be used to facilitate the processing of large numbers of test samples. Alternatively, single sample formats facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Flow cytometry can also be used to distinguish subpopulations of extracellular vesicles expressing different biomarkers. Typically, whole vesicles are incubated with antibodies that specifically bind to the biomarkers. The antibodies can be labeled, for example, with a fluorophore, isotope, or quantum dot to facilitate detection of the biomarkers. The vesicles are then suspended in a stream of fluid and passed through an electronic detection apparatus. In addition, fluorescence-activated cell sorting (FACS) can be used to sort a heterogeneous mixture of vesicles into separate containers. (See, e.g., Shapiro *Practical Flow Cytometry*, Wiley-Liss, 4$^{th}$ edition, 2003; Loken *Immunofluorescence Techniques in Flow Cytometry and Sorting*, Wiley, 2$^{nd}$ edition, 1990; *Flow Cytometry: Principles and Applications*, (ed. Macey), Humana Press 1$^{st}$ edition, 2007; herein incorporated by reference in their entireties.)

Cytometry by time-of-flight (CyTOF), also known as mass cytometry, is another method that can be used for detection of biomarkers in whole vesicles. CyTOF uses transition element isotopes as labels for antibodies, which are detected by a time-of-flight mass spectrometer. Unlike conventional flow cytometry, CyTOF is destructive to cells, but has the advantage that it can be used to analyze more cell markers simultaneously. See, e.g., Bendall et al. (2012) Trends in Immunology 33:323-332; Newell et al. (2012) Immunity 36(1):142-52; Ornatsky et al. (2010) J. Immunol. Methods 361 (1-2):1-20; Bandura et al. (2009) Analytical Chemistry 81:6813-6822; Chen et al. (2012) *Cell Mol. Immunol.* 9(4):322-323; and Cheung et al. (2011) Nat. Rev. Rheumatol. 7(9):502-3; herein incorporated by reference in their entireties.

In addition, multiplexed ion beam imaging (MIBI) can be used to distinguish subpopulations of vesicles carrying different biomarkers. MIBI uses secondary ion mass spectrometry to image antibodies that are tagged with isotopically pure elemental metal reporters. Not only can MIBI measure protein levels on individual vesicles, but also, the technique is capable of providing information about morphology and localization. Like CYTOF, MIBI is capable of analyzing a large number of biomarkers (e.g., up to 100) simultaneously over a five-log dynamic range. See, e.g., Angelo et al. (2014) Nat. Med. 20(4):436-442; Bodenmiller et al. (2016) Cell Syst. 2(4):225-238; and Levenson et al. (2015) Lab Invest. 95(4):397-405; herein incorporated by reference in their entireties.

Immunohistochemistry can be used to detect biomarkers on extracellular vesicles in resected tumor specimens. For example, immunohistochemical staining with labeled antibodies can be used to detect one or more biomarkers on vesicles. Antibodies conjugated to enzymes, which catalyze color-producing reactions with chromogenic, fluorogenic, or chemiluminescent substrates (e.g., alkaline phosphatase or peroxidase), are commonly used. Alternatively, immunohistochemical staining can be performed with antibodies conjugated to fluorophores (e.g., fluorescein or rhodamine) to visualize biomarkers. See, e.g., Dabbs *Diagnostic Immunohistochemistry: Theranostic and Genomic Applications*, Saunders, 3$^{rd}$ edition, 2010; Chu *Modern Immunohistochemistry* (Cambridge Illustrated Surgical Pathology) Cambridge University Press, 2009; Buchwalow et al. Immunohistochemistry: Basics and Methods, Springer, 1$^{st}$ Edition, 2010; and Ramos-Vara (2011) Methods Mol. Biol. 691:83-96; herein incorporated by reference in their entireties.

Antibodies that specifically bind to vesicular biomarkers can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). A protein marker antigen can be used to immunize a mammal, such as a mouse, rat, rabbit, guinea pig, monkey, or human, to produce polyclonal antibodies. If desired, a marker antigen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and Corynebacterium parvum are especially useful.

Monoclonal antibodies which specifically bind to a protein marker antigen can be prepared using any technique which provides for the production of antibody molecules by continuous cell lines in culture. These techniques include, but are not limited to, the hybridoma technique, the human B cell hybridoma technique, and the EBV hybridoma technique (Kohler et al., Nature 256, 495-97, 1985; Kozbor et al., J. Immunol. Methods 81, 31 42, 1985; Cote et al., Proc. Natl. Acad. Sci. 80, 2026-30, 1983; Cole et al., Mol. Cell Biol. 62, 109-20, 1984).

In addition, techniques developed for the production of "chimeric antibodies," the splicing of mouse antibody genes to human antibody genes to obtain a molecule with appropriate antigen specificity and biological activity can be used (Morrison et al., Proc. Natl. Acad. Sci. 81, 6851-55, 1984; Neuberger et al., Nature 312, 604-08, 1984; Takeda et al., Nature 314, 452-54, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332. Human monoclonal antibodies can be prepared in vitro as described in Simmons et al., PLoS Medicine 4(5), 928-36, 2007.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (Burton, Proc. Natl. Acad. Sci. 88, 11120-23, 1991).

Single-chain antibodies also can be constructed using a DNA amplification method, such as PCR, using hybridoma cDNA as a template (Thirion et al., Eur. J. Cancer Prey. 5, 507-11, 1996). Single-chain antibodies can be mono- or bispecific, and can be bivalent or tetravalent. Construction of tetravalent, bispecific single-chain antibodies is taught, for example, in Coloma & Morrison, Nat. Biotechnol. 15, 159-63, 1997. Construction of bivalent, bispecific single-chain antibodies is taught in Mallender & Voss, J. Biol. Chem. 269, 199-206, 1994.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., Int. J Cancer 61, 497-501, 1995; Nicholls et al., J. Immunol. Meth. 165, 81-91, 1993).

Antibodies which specifically bind to a marker antigen also can be produced by inducing in vivo production in the lymphocyte population or by screening immunoglobulin libraries or panels of highly specific binding reagents as disclosed in the literature (Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies can be purified by methods well known in the art. For example, antibodies can be affinity purified by passage over a column to which the relevant antigen is bound. The bound antibodies can then be eluted from the column using a buffer with a high salt concentration.

Antibodies may be used in diagnostic assays to detect the presence or for quantification of the markers in a biological sample. Such a diagnostic assay may comprise at least two steps; (i) contacting a sample comprising ovarian tissue or cells with the antibody and (ii) quantifying the antibody bound to the cellular marker antigen. The method may additionally involve a preliminary step of attaching the antibody, either covalently, electrostatically, or reversibly, to a solid support, before subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, or $^{125}I$, a fluorescent or chemiluminescent compound, such as fluorescein isothiocyanate, rhodamine, or luciferin, a fluorescent protein, such as a green fluorescent protein, red fluorescent protein, or yellow fluorescent protein, an enzyme, such as alkaline phosphatase, beta-galactosidase, or horseradish peroxidase, or a metal isotope, such as a rare earth element (e.g., cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) and yttrium (Y)). Any method known in the art for conjugating the antibody to the detectable moiety may be employed, including those methods described by Hunter et al., Nature, 144:945 (1962); David et al., Biochem., 13:1014 (1974); Pain et al., J. Immunol. Methods, 40:219 (1981); and Nygren, J. Histochem. and Cytochem. 30:407 (1982).

Treatment

Treatment of a patient, identified as having cancer by the methods described herein may comprise any suitable anti-cancer therapy including, for example, without limitation, surgery, radiation therapy, chemotherapy, targeted therapy, anti-angiogenic therapy, or immunotherapy, or any combination thereof.

For example, in the case of ovarian cancer, treatment by surgery may comprise a unilateral oophorectomy, a bilateral oophorectomy, or a salpingo oophorectomy.

Treatment by chemotherapy may comprise administering, for example, a platinum or a nonplatinum chemotherapeutic agent, or a combination thereof. Exemplary chemotherapeutic agents for treatment of ovarian cancer include paclitaxel, cisplatin, topotecan, doxorubicin, epirubicin, gemcitabine, docetaxel, carboplatin, and taxol. In one embodiment, chemotherapy comprises administering a platinum chemotherapeutic agent and taxol.

Treatment by immunotherapy may comprise administering, for example, an immune-modulatory agent, such as, but not limited to, an anti-PD1 agent such as pembrolizumab; an anti-PDL1 agent such as durvalumab; a Toll-like receptor 8 agonist such as motolimod; an anti-CTLA4 agent, such as tremelimumab, and an IDO1 inhibitor such as nivolumab, or an ovarian cancer vaccine or adoptive T cell transfer.

Treatment by targeted therapy may comprise administering, for example, one or more small molecule inhibitors or monoclonal antibodies such as, but not limited to, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib; Bcl-2 inhibitors, such as obatoclax and gossypol; PARP inhibitors, such as Iniparib and Olaparib; Pl3 kinase inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar); bromodomain and extra-terminal (BET) family inhibitors, such as JQ1, I-BET 151, I-BET 762, OTX-015, TEN-010, CPI-203, CPI-0610, RVX-208, and LY294002; and monoclonal antibodies, such as farletuzumab, mirvetuximab soravtansine, mirvetuximab soravtansine, mirvetuximab soravtansine, IMMU-132, DNIB0600A, DNIB0600A, demcizumab (OMP-21M18), and monalizumab. In certain embodiments, targeted therapy comprises administering a poly-(ADP)-ribose polymerase (PARP) inhibitor, a P13 kinase inhibitor, or a targeted bromodomain and extra-terminal (BET) family inhibitor, or a combination thereof.

Treatment by anti-angiogenic therapy may comprise administering a vascular endothelial growth factor (VEGF) inhibitor such as bevacizumab.

It will be apparent to one of ordinary skill in the art that various changes and modifications can be made without departing from the spirit or scope of the invention.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention.

EXAMPLE 1

Noninvasive Preparation of Intact Exosomes on a Solid Substrate for Nanoscale FTIR Spectromicroscopic Characterization It is well-documented that tumor cells, including those derived from ovarian carcinomas, exhibit numerous changes not only in the conformation of DNA and protein structures, but also in their lipid membrane, such as increased outer leaflet presentation of phosphatidylserine (PS) and altered membrane fluidity. These alterations have been linked to critical tumor processes such as immune suppression and metastasis. It has further been demonstrated that Fourier transform infrared (FTIR) spectromicroscopy, which provides fingerprint-like spectra derived from the characteristic vibrational frequencies of chemical bonds and chemical functional groups, is capable of differentiating between normal and malignant ovarian tissue ovarian cancer cells.

Tumor-derived exosomes, small membrane-bound extra-cellular vesicles 40-200 nm in diameter, share many underlying physico-chemical characteristics with their parental cells, and are continually shed into circulation. Thus, exosomes are a highly promising platform for personalized cancer diagnostics. Due to their noninvasive, nondestructive nature, mid-infrared vibrational spectroscopy-based technologies have been suggested for use as a screen for candidate tumor-derived exosomes prior to further characterization by other techniques such as micro-mass spectrometry and micro-sequencing, which afford greater chemical specificity. However, purified, immobilized exosome sample preparation remains challenging due to the osmotic susceptibility of intact exosomes. Beekman et al. circumvent this problem through an extensive capture and fixation procedure, at the cost of directly chemically altering the exosomes. Kim et al. use a direct drying from exosomes-in-PBS procedure, but note difficulties relating to the presence of localized contaminating biomolecules altering exosome infrared spectra. In our hands, this protocol has also resulted in the formation of infrared-active sheets of phosphate salts.

Here, we present a protocol for the preparation of intact, unfixed exosomes for downstream single-particle analysis.

Methods

4T1 Cell Culture

4T1 cells were purchased from the American Tissue Culture Collection (CRL-2539), and stored in liquid nitrogen. Cells were propagated in Roswell Park Memorial Institute (RPMI 1640) medium supplemented with 10% fetal calf serum for two passages prior to exosome harvesting.

Exosome Isolation

Media supernatant was harvested from 4T1 cell cultures, then spun down for 5 minutes at 300 g, then 20 minutes at 3000 g in order to remove cellular debris. Each time the supernatant was removed and saved, while the pellet was discarded. Exosomes were isolated by Exosome Total Isolation Chip, as in (Liu et al. 2017), followed by dilution and washing in Hank's buffered salt solution (HBSS). Prior to sample preparation, exosome aliquots were spiked to a final concentration of 2 mM $CaCl_2$, or 2 mM $CaCl_2$+25 ng/mL annexin V. Annexin V was obtained courtesy of Dr. Jonathan Tait, and manufactured as previously described (Blankenberg et al. 1999).

Slide/Sample Preparation

Gold on titanium on glass slides were cleaned using 60% acetone, 40% ethanol, and rinsed 5x in Milli-q water prior to plasma cleaning. After ~4 hours, each slide was placed in humidified chambers. Humidified chambers were prepared using 15 mM tissue culture dishes (Falcon 08-772B). The interior edges were lined with rolled strips of 11×21 cm Kimtech Science Kimwipes (Kimberly Clark 06-666A) that had been dampened with Milli-q water, with excess water removed by gentle brushing against the rim of the Milli-q container (50 mM Falcon conical centrifuge tube, Corning 352070). 10 µL of exosome sample, either with or without annexin V, were dropped into the center of each slide.

The humidified chambers were then capped, and finally sealed with parafilm strips. Slides were then allowed to sit at room temperature overnight. The following morning, humidified chambers were unsealed. The slides were gently but quickly rinsed in Milli-q water in order to remove residual media and salts, though it was noted that excessive rinsing rapidly leads to exosome lysis. Excess water was wicked away from the slide edge using a kimwipe, and residual water was removed by gentle air-drying using a house air line attached to a 25 mm 0.22 um syringe filter (09-740-113) with a tip-snipped 100 μL pipette tip on the distal end.

Imaging

SINS data was acquired using the custom built apparatus at Lawrence Berkeley National Lab's (LBNL) Advanced Light Source (ALS) Beamline 5.4, as described in (Bechtel et al. 2014), and either PtSi-NCH (NanoAndMore PtSi-NCH-50) or (HQ:NSC18/Cr—Au—50) AFM tips. Dark field imaging was performed using a Thermo Scientific DXR Raman Microscope with brightfield/darkfield reflection illumination.

Results

There were three primary considerations for our preparation of exosomes: 1) Exosomes should be dispersed enough for single-exosome imaging, 2) Exosomes should be intact, rather than lysed, and 3) Exosomes should be generally free of visible contaminants, such as residual salts.

Figure 5A:
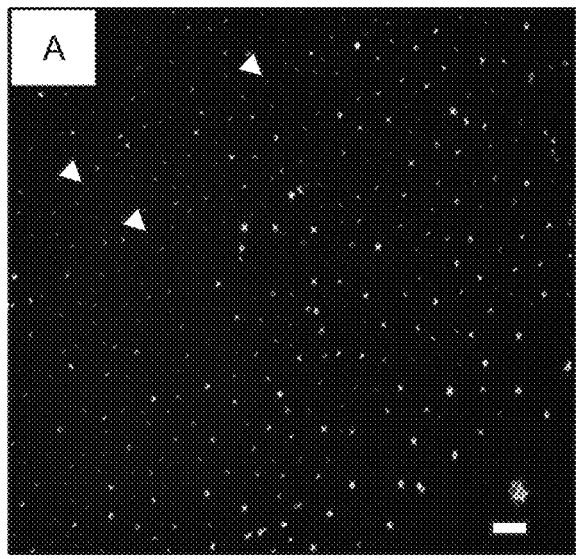
FIGS. 5A-5G show dark field microscopy of purified exosomes dispersed in (FIG. 5A) 25 ng/mL annexin V+2 mM $CaCl_2$ or (FIG. 5B) in 2 mM $CaCl_2$. scale bars=1 μm.
Figure 5B:
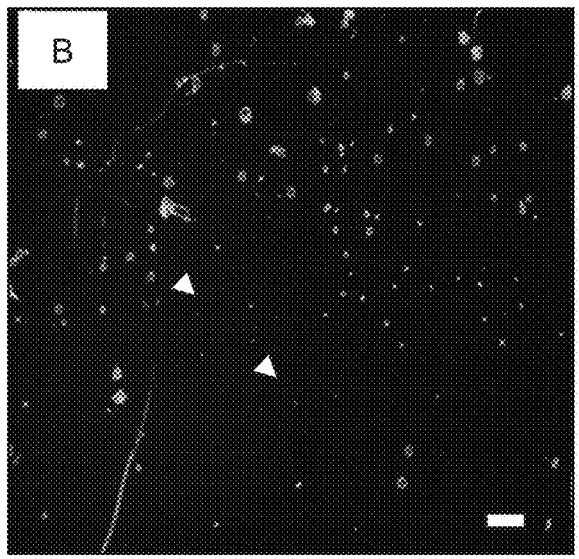
Figure 5C:
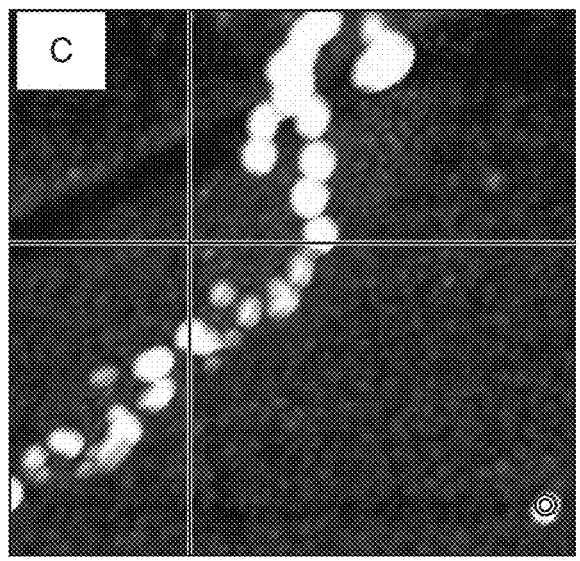
Figure 5D:
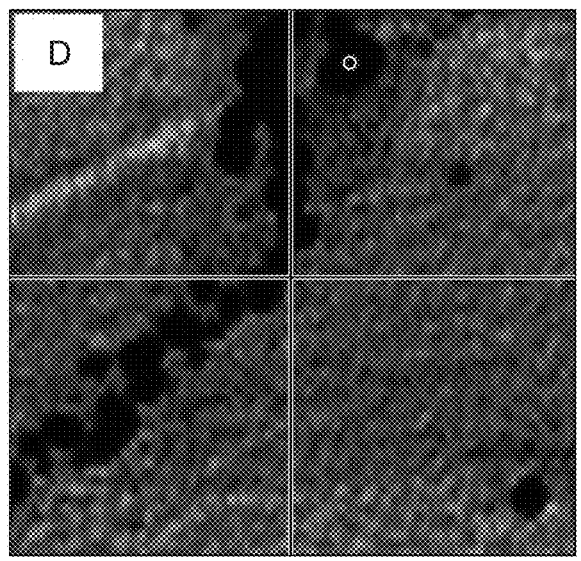

We performed darkfield microscopy on our samples, in comparison to annexin V-coated exosome samples, in order to identify the degree of dispersal. In comparison to annexin V-coated samples, our preparation did exhibit increased aggregation (FIGS. 5A, 5B). Further examination by AFM uncovered the formation of long strings of intact exosomes (FIG. 5C), each of which was shown to have infrared-active absorbance features (FIG. 5D). Notably, the surrounding regions are generally free of infrared absorbance features, strongly suggesting that residual salts (especially infrared-active phosphate salts) and other biological materials have been adequately removed.

Figure 5E:
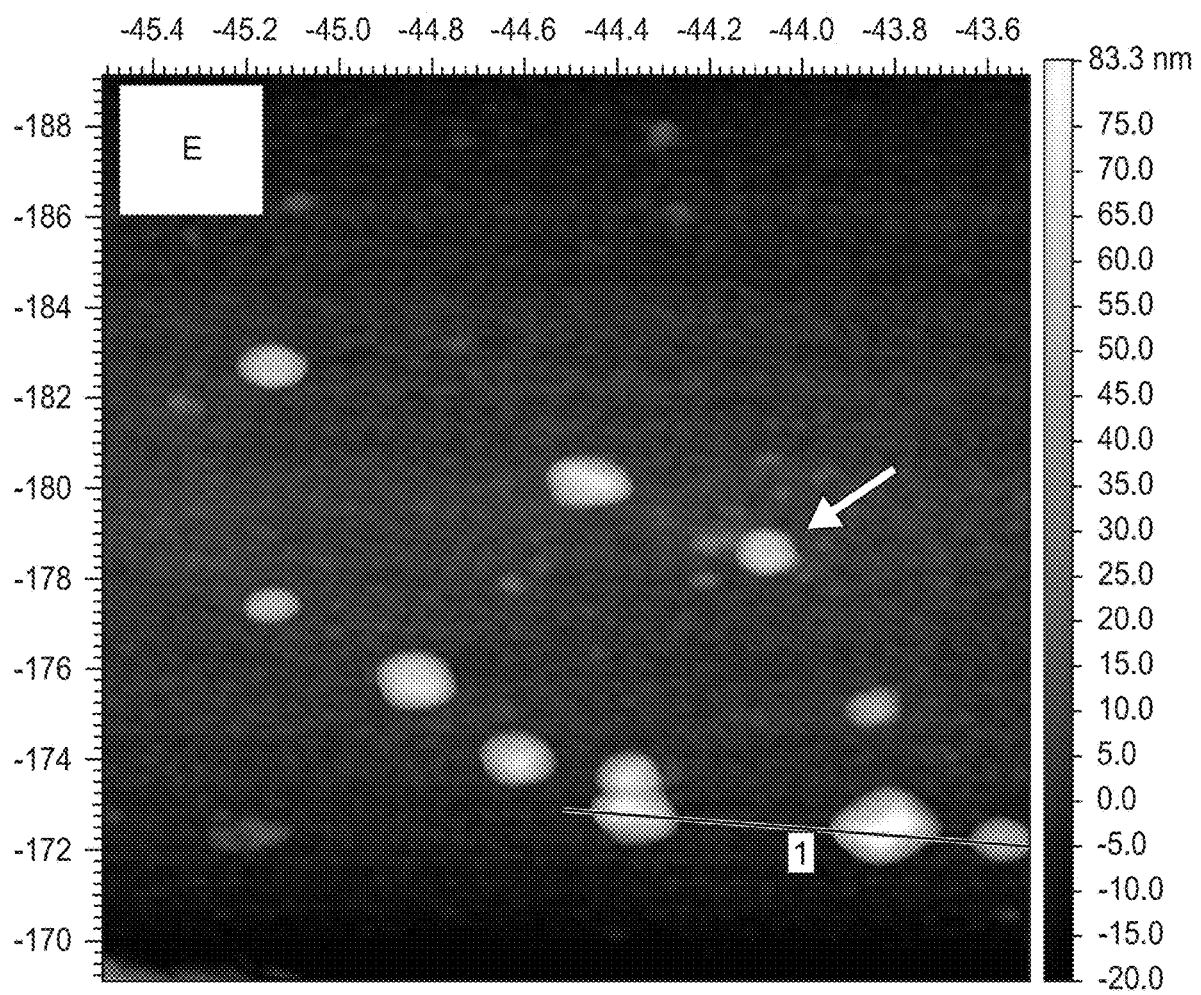
Figure 5F:
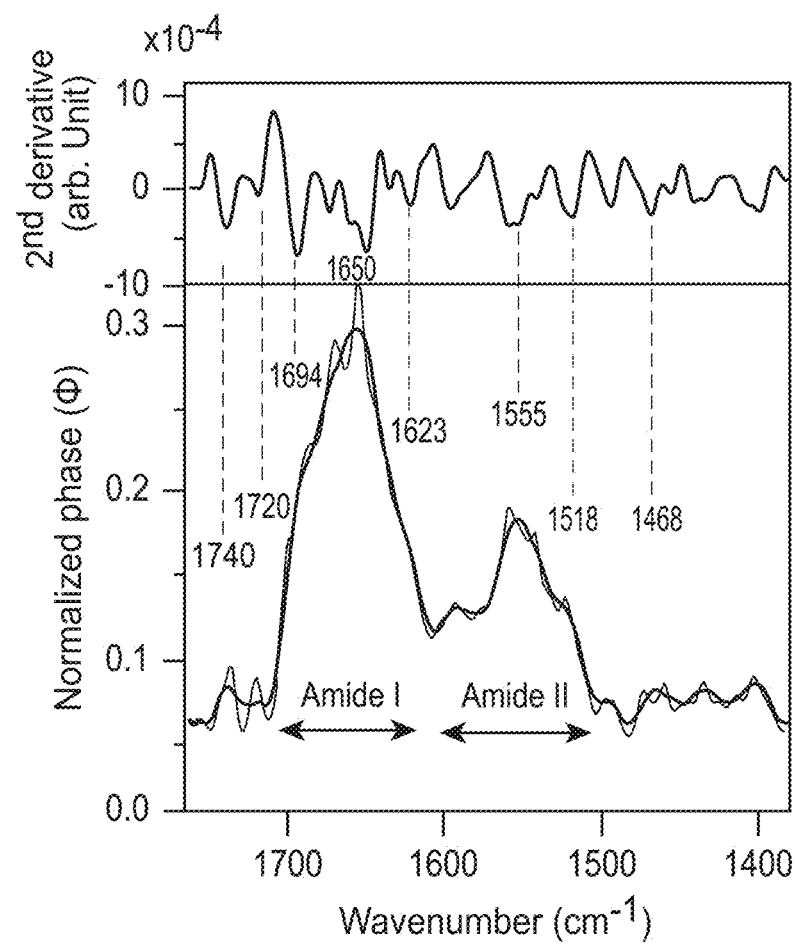
Figure 5G:
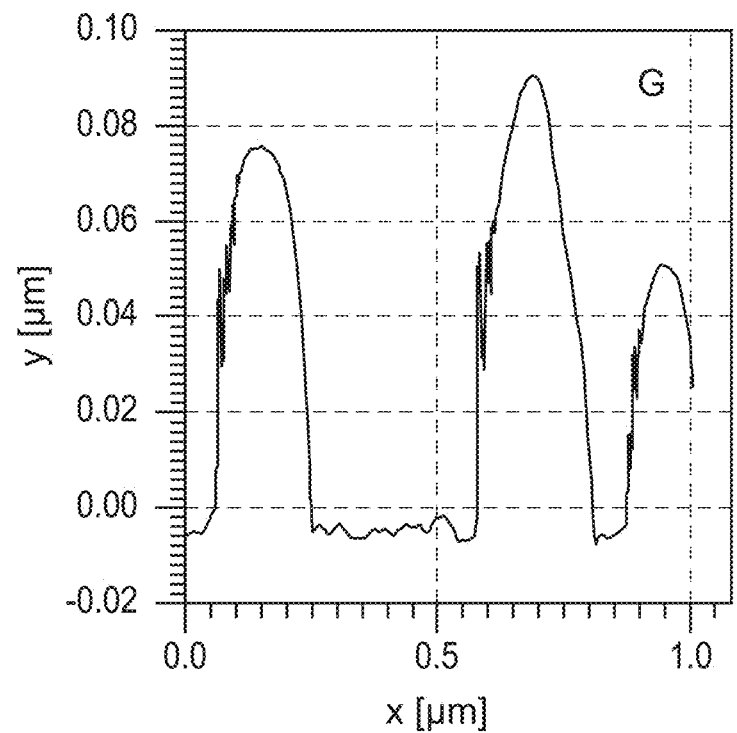

Even for samples in which aggregation was observed, there were plentiful areas of dispersed single exosomes (FIG. 5E). From these regions, we were able to obtain single-exosome SINS spectra (FIG. 5F), with clear peaks at 1738 $cm^{-1}$, representing non-peptide carbonyl stretching bands, 1657 $cm^{-1}$ representing amide I absorption bands, and 1553 $cm^{-1}$, representing amide II absorption bands. Smaller, subtler features between ~1400 and 1500 $cm^{-1}$ may represent lipid C-H bending modes, but are not easily distinguishable from background noise. We also found that the amide I peak at 1657 $cm^{-1}$ is blue-shifted relative to the normal bulk amide peak, which is typically ~1640-1650 $cm^{-1}$, and occupies a region commonly associated with p-turn peptide structures. Topographical quantification (FIG. 5G) was in approximately the same size range as our initial size assessments.

REFERENCES

1. Lea, Jayanthi, et al. "Detection of phosphatidylserine-positive exosomes as a diagnostic marker for ovarian malignancies: a proof of concept study." *Oncotarget* 8.9 (2017): 14395.
2. Birge, R. B., et al. "Phosphatidylserine is a global immunosuppressive signal in efferocytosis, infectious disease, and cancer." *Cell death and differentiation* 23.6 (2016): 962.
3. Funaki, Naomi Omichi, et al. "Membrane fluidity correlates with liver cancer cell proliferation and infiltration potential." *Oncology reports* 8.3 (2001): 527-532.
4. Grzelak, M. M., et al. "Diagnosis of ovarian tumour tissues by SR-FTIR spectroscopy: A pilot study." *Spectrochimica Acta Part A: Molecular and Biomolecular Spectroscopy* 203 (2018): 48-55.
5. Li, Lei, et al. "Characterization of ovarian cancer cells and tissues by Fourier transform infrared spectroscopy." *Journal of ovarian research* 11.1 (2018): 64.
6. Caby, Marie-Pierre, et al. "Exosomal-like vesicles are present in human blood plasma." *International immunology* 17.7 (2005): 879-887.
7. Beekman, Pepijn, et al. "Immuno-capture of extracellular vesicles for individual multi-modal characterization using AFM, SEM and Raman spectroscopy." *Lab on a Chip* 19.15 (2019): 2526-2536.
8. Kim, Sally Yunsun, et al. "None of us is the same as all of us: resolving the heterogeneity of extracellular vesicles using single-vesicle, nanoscale characterization with resonance enhanced atomic force microscope infrared spectroscopy (AFM-IR)." *Nanoscale Horizons* 3.4 (2018): 430-438.
9. Liu F, Vermesh O, Mani V, Ge T J, Madsen S J, Sabour A, Hsu E C, Gowrishankar G, Kanada M, Jokerst J V, Sierra R G, Chang E, Lau K, Sridhar K, Bermudez A, Pitteri S J, Stoyanova T, Sinclair R, Nair V S, Gambhir S S, Demirci U. The Exosome Total Isolation Chip. ACS Nano. 2017 Nov. 28; 11(11):10712-10723. PMID: 29090896
10. Blankenberg FG, Katsikis PD, Tait JF, Davis RE, Naumovski L, Ohtsuki K, Kopiwoda S, Abrams M J, Strauss H W. Imaging of apoptosis (programmed cell death) with 99 mTc annexin V. J Nucl Med. 1999 January; 40(1):184-91. PMID: 9935075

EXAMPLE 2

Discovery and Identification of Spectral Biomarker Candidates from Exosomes Derived from Cell Culture Exosomes are isolated from the cell culture medias of ovarian carcinoma panel cell lines ATCC TCP-1021, benign ovarian teratoma ATCC CRL-7826, and low passage human ovarian surface epithelial cells (ScienCell #7310) via serial ultracentrifugation. Quantification of exosomes is performed using a NanoSight LM10 Nanoparticle tracker.

Figure 3A:
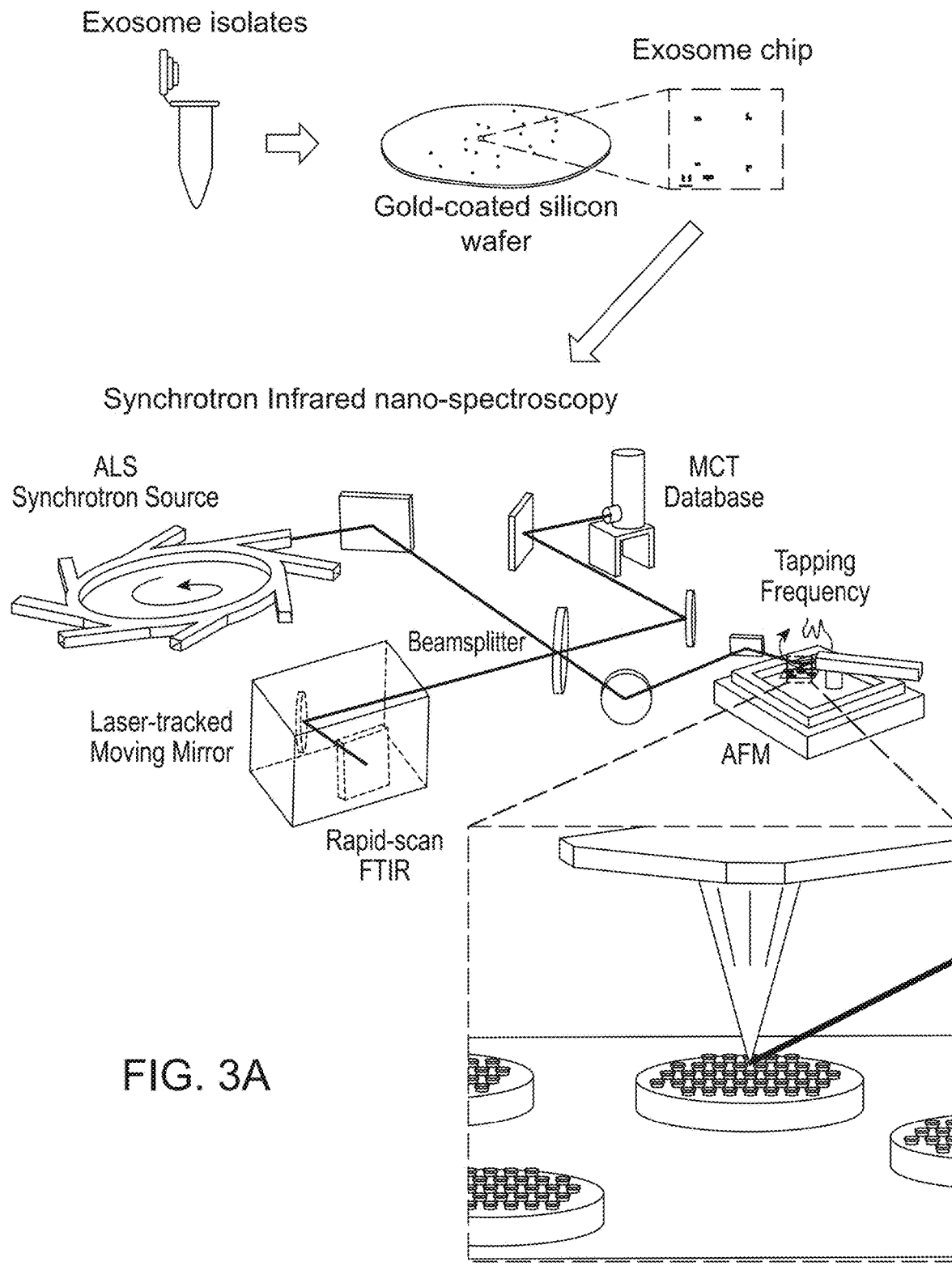
FIG. 3A shows schematics of the proposed experimental plan using synchrotron infrared nanospectroscopy as a label-free biochemical probe.
Figure 3B:
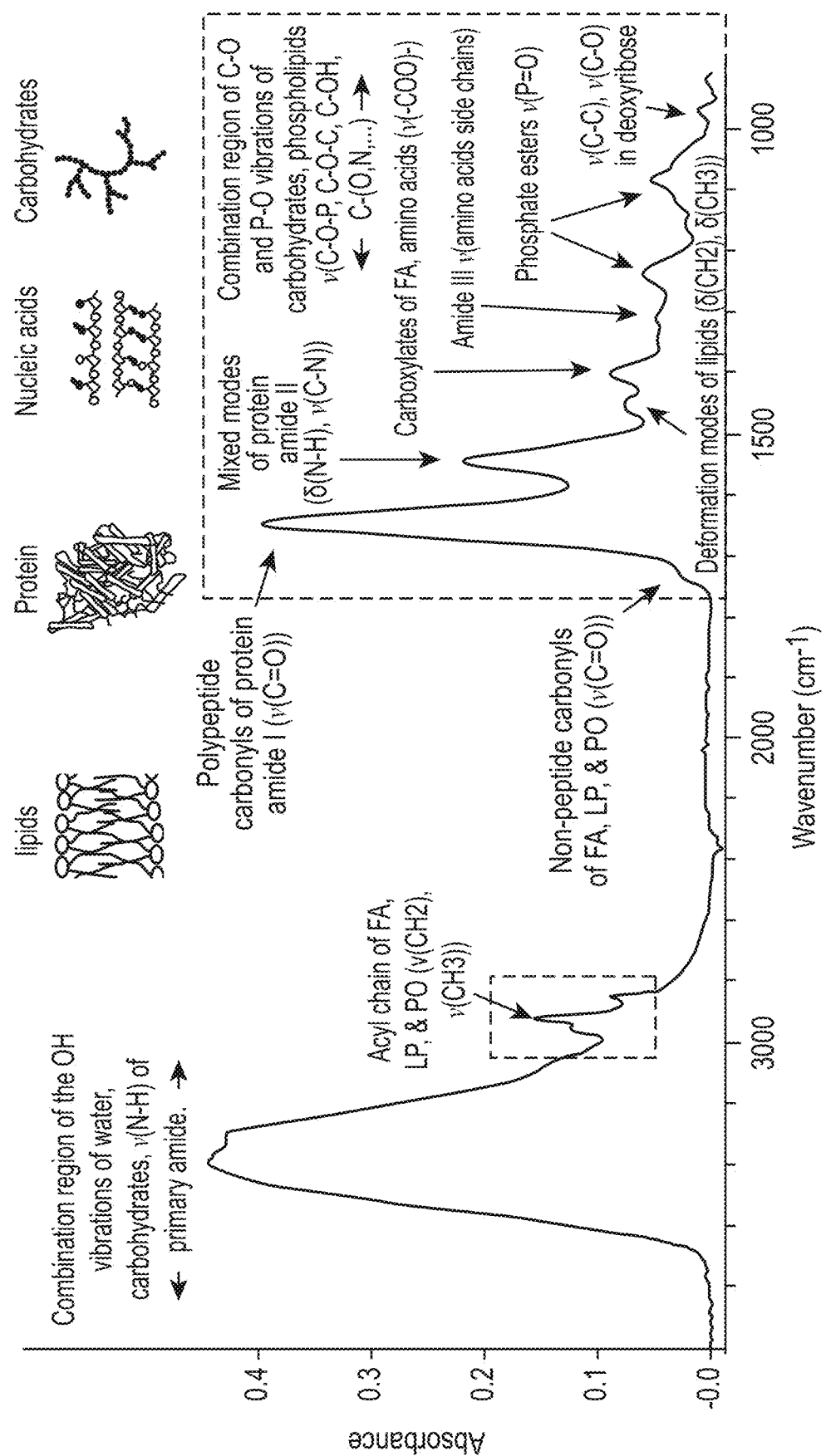
FIG. 3B shows a typical infrared spectrum with labels highlighting absorption peaks associated with constituent macromolecules.
Figure 4A:
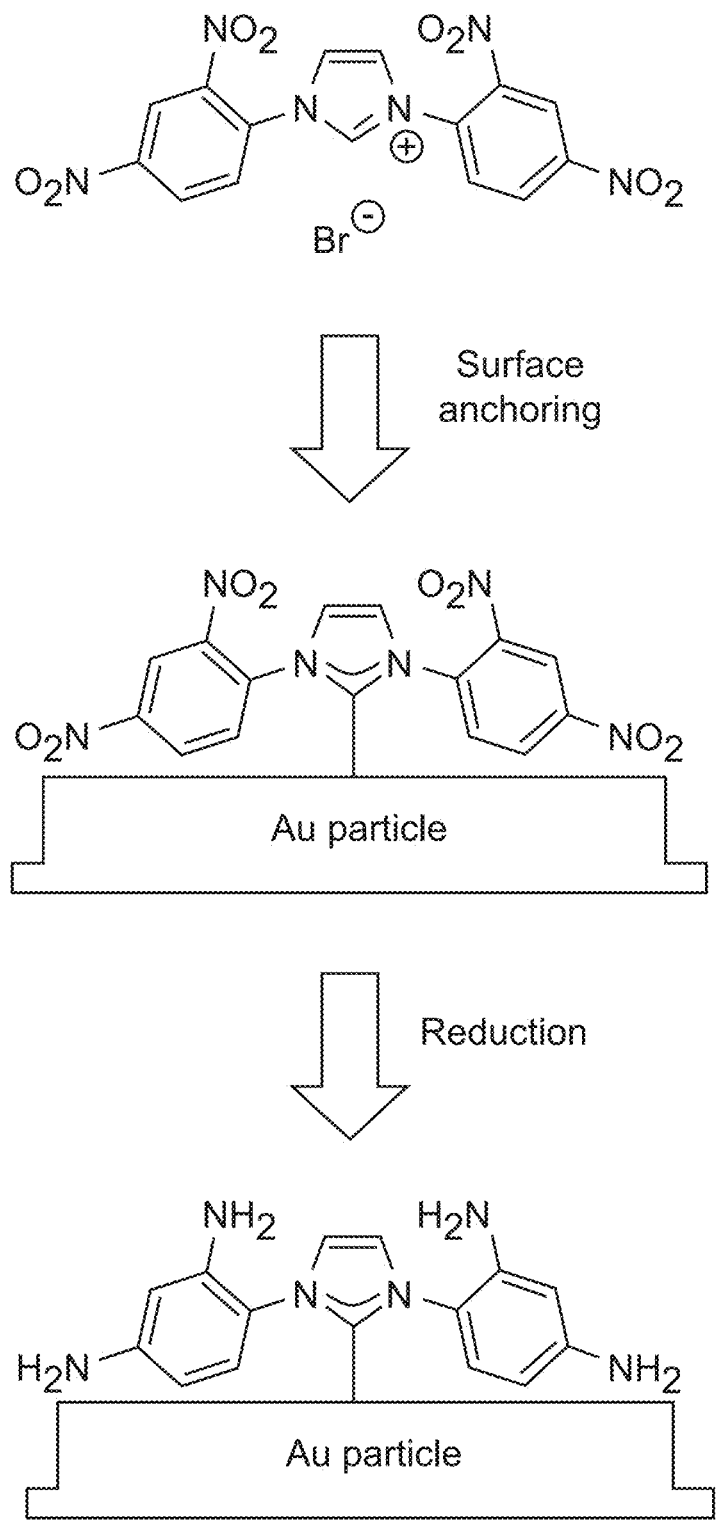
FIGS. 4A-4C show an example demonstrating synchrotron nanospectroscopy capabilities at the Advanced Light Source (ALS) synchrotron facility beamline 5.4.
Figure 4B:
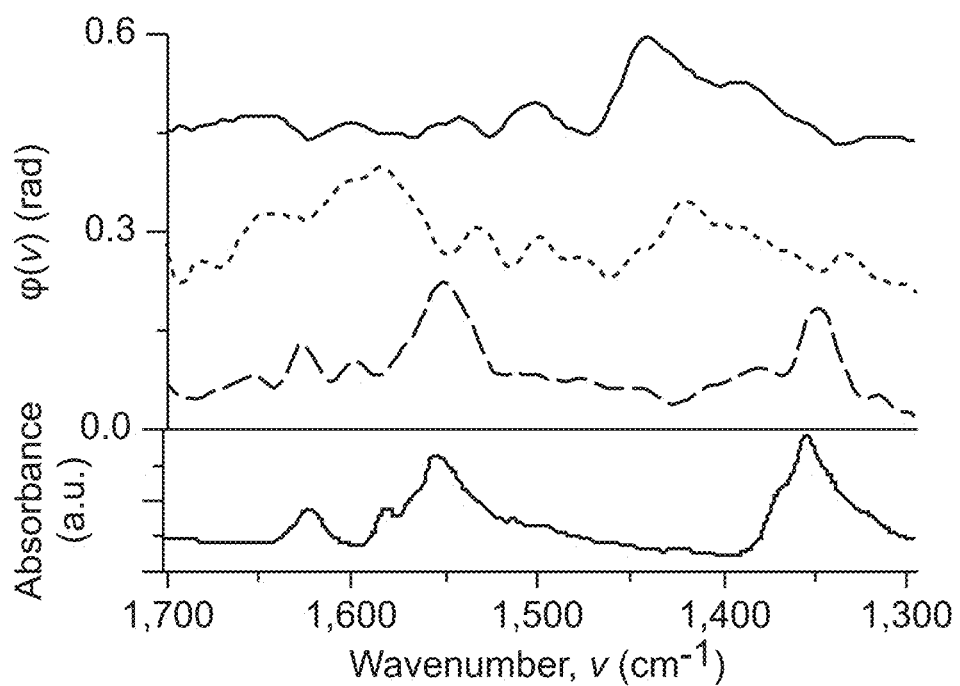
Figure 4C:
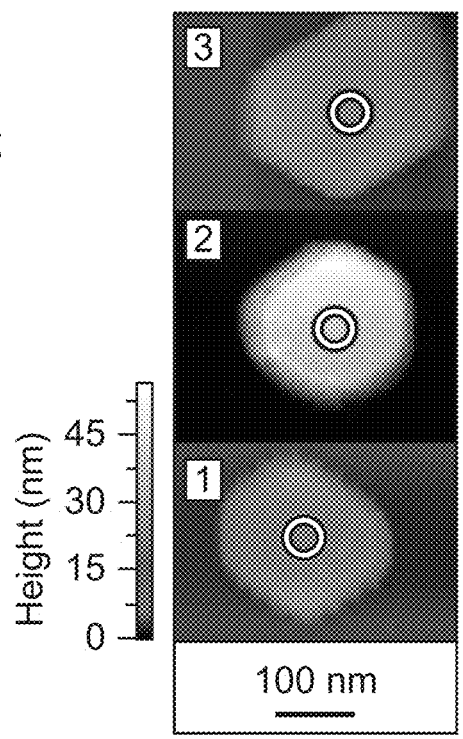

All nano-spectra are obtained at the infrared beamline at the Advanced Light Source (ALS) synchrotron facility at Lawrence Berkeley National Laboratory (LBNL) (FIG. 3). This is a national DOE-funded user facility, for which user access is granted through the externally peer-reviewed ALS General User Proposal (GUP) program. While the final clinical diagnosis can occur on relatively narrow-band sources (such as quantum cascade laser-based devices), a high-brightness, broadband synchrotron source is critical for the initial physico-chemical characterization of exosomes. The infrared beamlines (1.4 and 5.4) at this facility are capable of accomplishing the required work. The capabilities and advantages of the nano-spectroscopy technology at the facility is demonstrated in FIG. 4.

Since PS exposure is a major immunosuppressive force both locally and systemically and is commonly presented to the external plasma membrane of tumor cells, we independently assess PS exposure as a biomarker by incubating exosomes with 100 nM annexin V and 2 mM $Ca^{2+}$. Annexin V cooperatively binds PS-rich surfaces in a calcium-dependent manner, arranging in sheets, causing local increases in membrane stiffness, and causing bilayer deformation, all of which is detectable by vibrational spectroscopy.

Markers candidates are discovered using multivariate curve resolution, and further identified via curation by existing literature.

EXAMPLE 3

Discovery and Identification of Spectral Biomarkers from Exosomes Derived from Serum $5 \times 10^6$ ovarian cancer panel cells are implanted into the flank of athymic female nude mice, in groups of 5. Tumor growth is carefully monitored, and once the tumor is palpable, mice are sacrificed, blood is drawn, and total exosomes are isolated via serial centrifugation from plasma. Exosomes are similarly isolated from control nude mice. Tumor-derived exosomes are separated from normal exosomes by selecting for PS+ exosomes using fluorescent-labeled annexin V followed by fluorescence-associated cell sorting (FACS). After separation, PS+ exosomes are separated into two groups. One is treated with EDTA, causing detachment of annexin V from labeled exosomes. The other group is retained in its annexin V-bound form, to allow for further characterization of the effect of annexin V-binding on membrane properties. Separated exosomes are quantified, spotted onto a gold slide substrate, then air-dried for spectra acquisition.

Similar to the approach in Example 2, marker candidates are discovered using multivariate curve resolution, then curated against the existing body of literature.

What is claimed is:

1. A method for determining the presence of one or more cancer biomarkers in a sample, the method comprising:
obtaining a biological sample comprising extracellular vesicles from a patient suspected of having cancer;
dispersing intact extracellular vesicles on a substrate;
recording mid-infrared spectra with single-vesicle resolution of individual cancer-derived extracellular vesicles, or individual subpopulations of cancer-derived extracellular vesicles in the biological sample to determine if a cancer biomarker is present; using mid-infrared vibrational spectroscopy performed with a narrow-band mid-infrared light source or a broadband mid-infrared light source, selected from a (i) synchrotron source including synchrotron infrared nanospectroscopy (SINS) and (ii) atomic force microscope Fourier transform infrared (AFM-FTIR) spectrometer.

2. The method of claim 1, further comprising medical imaging of the patient if the spectral chemical fingerprint indicates the presence of one or more cancer biomarkers.

3. The method of claim 1, further comprising treating the patient with radiation therapy, chemotherapy, targeted therapy, anti-angiogenic therapy, or immunotherapy, or any combination thereof if one or more cancer biomarkers are determined to be present.

4. The method of claim 1, wherein said detection of the spectral chemical fingerprint comprises comparing the single-vesicle-resolution spectra from cancer-derived extracellular vesicles, or from a subpopulation of cancer-derived extracellular vesicles from the biological sample, to reference mid-infrared spectra from reference cancer-derived extracellular vesicles from a sample obtained from a subject with the cancer to determine if the spectra of the single cancer-derived extracellular vesicles from the biological sample match the reference spectrum in a spectral region corresponding to the spectral chemical fingerprint.

5. The method of claim 1, wherein the cancer is ovarian cancer.

6. The method of claim 5, wherein the reference mid-infrared spectra are from reference cancer-derived extracellular vesicles from a sample obtained from a subject with early stage ovarian cancer at stage I or stage II or late stage ovarian cancer at stage III or stage IV.

7. The method of claim 1, further comprising comparing the mid-infrared single-vesicle-resolution spectra from cancer-derived extracellular vesicle, or from a subpopulation of cancer-derived extracellular vesicles, from the biological sample to a control mid-infrared spectra of control extracellular vesicles from a control sample obtained from a control subject not having the cancer, wherein the spectral chemical fingerprint comprises at least one spectral difference between the spectra of the single cancer-derived extracellular vesicle or the subpopulation of cancer-derived extracellular vesicles from the biological sample and the spectra of the control extracellular vesicles from the control sample.

8. The method of claim 7, wherein the spectral difference is an increase or decrease in absorbance at a same wavenumber or a shift in position of an absorption peak in the mid-infrared spectrum of the biological sample compared to the control mid-infrared spectrum.

9. The method of claim 8, wherein the spectral difference is in a spectral region ranging between wavenumbers from about 2800 $cm^{-1}$ to about 3000 $cm^{-1}$, about 1500 $cm^{-1}$ to about 1750 $cm^{-1}$, or about 900 $cm^{-1}$ to about 1300 $cm^{-1}$.

10. The method of claim 1, wherein said detection of the spectral chemical fingerprint is automated by using a multivariate classification algorithm.

11. The method of claim 1, wherein the cancer-derived extracellular vesicle is an intact, unfixed and not permeabilized cancer-derived extracellular vesicle.

12. The method of claim 1, wherein the one or more cancer biomarkers comprise phosphatidylserine in the cancer-derived extracellular vesicle membrane, which is detected by contacting the extracellular vesicles in the biological sample with a phosphatidylserine binding agent such that the phosphatidylserine binding agent binds to the phosphatidylserine in the membranes of said extracellular vesicles.

13. The method of claim 12, wherein the phosphatidylserine binding agent is annexin V.

14. The method of claim 12, wherein a phosphatidylserine positive cancer-derived extracellular vesicle comprising bound phosphatidylserine binding agent is detectably labeled with the fluorescent label and isolated by fluorescence-associated cell sorting (FACS).

15. A method for determining the presence of one or more cancer biomarkers in a sample, the method comprising:
obtaining a biological sample comprising extracellular vesicles from a patient suspected of having cancer;
recording mid-infrared spectra with single-vesicle resolution from cancer-derived extracellular vesicles, or from a subpopulation of individual cancer-derived extracellular vesicles, in the biological sample to determine if a cancer biomarker is present,
wherein the one or more cancer biomarkers comprise phosphatidylserine in the cancer-derived extracellular vesicle membrane, which is detected by contacting the extracellular vesicles in the biological sample with a phosphatidylserine binding agent such that the phosphatidylserine binding agent binds to the phosphatidylserine in the membranes of said extracellular vesicles, and
using mid-infrared vibrational spectroscopy to detect increases in membrane stiffness or bilayer deformation caused by binding of the phosphatidylserine binding agent to the phosphatidylserine.

16. The method of claim 1, further comprising isolating a cancer-derived extracellular vesicle, if present, from the biological sample, wherein the cancer-derived extracellular vesicle is a phosphatidylserine positive cancer-derived extracellular vesicle and is isolated by positive selection for extracellular vesicles comprising annexin V bound to the phosphatidylserine.

17. The method of claim 1, wherein the dispersing step comprises dispersing the cancer-derived extracellular vesicles in the presence of $Ca^{2+}$ and annexin V.

18. The method of claim 1, further comprising performing an immunoassay to detect the one or more biomarkers, wherein the immunoassay is selected from the group consisting of an enzyme-linked immunosorbent assay (ELISA), an immunofluorescent assay (IFA), an immune-polymerase chain reaction assay, an electro-chemiluminescence immunoassay (ECLIA), and a radioimmunoassay (RIA).

* * * * *